United States Patent [19]
Malikayl et al.

[11] Patent Number: 6,069,232
[45] Date of Patent: May 30, 2000

[54] POLYFLUOROALKYL TRYPTOPHAN TRIPEPTIDE THROMBIN INHIBITORS

[75] Inventors: J. Anthony Malikayl, Cincinnati, Ohio; Joseph P. Burkhart, Plainfield, Ind.; Robert J. Broersma; Norton P. Peet, both of Cincinnati, Ohio

[73] Assignee: Hoechst Marion Roussel, Inc., Bridgewater, N.J.

[21] Appl. No.: 08/698,931

[22] Filed: Aug. 26, 1996

Related U.S. Application Data

[63] Continuation-in-part of application No. 08/566,615, Dec. 4, 1995, abandoned
[60] Provisional application No. 60/004,755, Oct. 2, 1995.

[51] Int. Cl.$^7$ ..................................................... C07K 5/08
[52] U.S. Cl. .............................. 530/331; 514/18; 514/19; 548/535; 548/496
[58] Field of Search ................. 514/18, 19; 530/331; 548/496, 535

[56] References Cited

U.S. PATENT DOCUMENTS

| | | | |
|---|---|---|---|
| 4,061,625 | 12/1977 | AfEkenstam et al. | 260/112.5 |
| 4,216,142 | 8/1980 | Ali | 260/112.5 |
| 4,217,269 | 8/1980 | Cole | 260/112.5 |
| 4,221,706 | 9/1980 | Ali et al. | 260/112.5 |
| 4,247,454 | 1/1981 | AfEkenstam et al. | 260/112.5 |
| 4,275,153 | 6/1981 | Gagiulo | 435/13 |
| 4,318,904 | 3/1982 | Shaw et al. | 424/177 |
| 4,399,065 | 8/1983 | Bajusz et al. | 260/112.5 |
| 4,450,105 | 5/1984 | Nagasawa et al. | 260/112.5 |
| 4,478,745 | 10/1984 | Bajusz et al. | 260/112.5 |
| 4,607,047 | 8/1986 | Debay | 514/428 |
| 4,643,991 | 2/1987 | Digenis et al. | 514/18 |
| 4,703,036 | 10/1987 | Bajusz et al. | 514/18 |
| 4,720,484 | 1/1988 | Vincent | 514/18 |
| 4,762,821 | 8/1988 | Nestor | 514/19 |
| 4,816,560 | 3/1989 | VErdini et al. | 530/323 |
| 4,816,562 | 3/1989 | Nagasawa et al. | 530/331 |
| 4,826,814 | 5/1989 | Sawayama et al. | 514/18 |
| 4,880,780 | 11/1989 | Trainor et al. | 514/18 |
| 4,929,602 | 5/1990 | Harker et al. | 514/18 |
| 4,980,349 | 12/1990 | Roger et al. | 574/231.8 |
| 5,053,392 | 10/1991 | Klein et al. | 514/18 |
| 5,391,705 | 2/1995 | Neises et al. | 530/331 |

FOREIGN PATENT DOCUMENTS

| | | |
|---|---|---|
| 0185390 | 6/1986 | European Pat. Off. |
| 0192135 | 8/1986 | European Pat. Off. |
| 0195212 | 8/1986 | European Pat. Off. |
| 0410411 | 1/1991 | European Pat. Off. |
| 0503203 | 3/1991 | European Pat. Off. |
| 0498508 | 2/1992 | European Pat. Off. |
| 2287027 | 9/1995 | United Kingdom. |
| 9425051 | 4/1994 | WIPO. |

OTHER PUBLICATIONS

Pitzele, Barrett S., J. Med. Chem., 1994, vol. 37, pp. 888–896.
Shuman, Robert T., J. Med. Chem., 1993, vol. 36, pp. 314–319.
Chem. Abst., vol. 110, p. 709, 1989, No. 76058: Angliker, "Synthesis and properties of peptidyl derivatives of arginylfluoromethames" (Biochemical Journal), vol. 256, No. 2, pp. 481–486.
Angeliker et al, Biochem. J. vol. 256, No. 2, pp. 481–486 (1988).
Gelb et al, "Fluoro Ketone Inhibitors of Hydrolytic Enzymes", Biochemistry, vol. 24, No. 8, pp. 1813–1817, (1985).
Sham et al, "Highly potent and specific inhibitors of human renin", FEBS Letters, vol. 220, No. 2, pp. 299–301, 1987.
Chemical Abstracts, vol. 107, 1987, No. 40336Y, p. 758, Stueber, M: Oigopeptidylarginniol derivatives and their homologs, there use as antithrombics and agents containing them (Abstract of EP 0 192 138).
Shuman et al, Proceedings of the 12th American Peptide Symposium, pp. 801–802 (1991).
Kolb et al, Tetrahedron Letters vol. 27, No. 14, pp. 1579–1582 (1986).
Kolb et al, Tetrahedron Letters vol. 27, No. 37, pp. 4437–4440 (1986).
Kolb et al, Liebigs Ann. Chem. pp. 1–6 (1990).
Peet, N.P., et al J. Med. Chem. 33, pp. 394–407 (1990).
Neises, B., et al, Journal of the International Society of Thrombosis and Haemostatis, Abstracts p. 1290, (1991).
Ranganathan et al, Nitroethylene: A Stable, Clean and Reactive Agent for Organic Synthesis, J. Org. Chem., 45, pp. 1185–1189 (1980).
Berliner, Lawrence J., et al, "Physical Evidence for an Apolar Binding Site Near the Catalytic Center of Human α–Thrombin†", Biochemistry, vol. 16, No. 21, 1977, pp. 4622–4626.
Malikayl et al, *Biochemistry*, vol. 36, pp. 1034–1040, (1997).

Primary Examiner—Robert J. Hill, Jr.
Assistant Examiner—David Lukton
Attorney, Agent, or Firm—T. Helen Payne

[57] ABSTRACT

This invention relates to polyfluoroalkyl tryptophan tripeptides and to compositions containing them. The compounds are highly selective thrombin inhibitors which provide anticoagulant effects useful in the treatment of thrombin conditions and in preventing the coagulation of stored whole blood and blood products.

22 Claims, No Drawings

POLYFLUOROALKYL TRYPTOPHAN TRIPEPTIDE THROMBIN INHIBITORS

This application is a continuation-in-part of application Ser. No. 08/566,615, filed Dec. 4, 1995, now abandoned which claims the benefit of U.S. Provisional Application No. 60/004,755, filed Oct. 2, 1995.

BACKGROUND OF THE INVENTION

Anticoagulants are useful therapeutic agents in the pharmacological treatment of, for example, acute deep venous thrombosis, pulmonary embolism, acute arterial embolization of the extremities, myocardial infarction, stroke, restenosis and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

A current method for the treatment and prophylaxis of thrombotic diseases involves the inhibition of thrombin activity or thrombin formation, thus preventing clot formation. It is known in the art that the tripeptide (D)-Phe-Pro-Arg is a thrombin catalytic site inhibitor. Moreover, U.S. Pat. No. 5,391,705 describes polyfluorinated tripeptides which inhibit both thrombin and trypsin. Likewise, PCT Patent Application Publication No. WO 94/25051 describes thrombin inhibitors in which arginine is replaced with aminocyclohexyl moieties. However, the art does not appear to suggest that the tripeptide will retain antithrombin activity when tryptophan is substituted for arginine at the $P_1$ position of the enzyme recognition site.

Applicants have discovered that when tryptophan is substituted for arginine or derivatives of arginine at the $P_1$ position of known pentafluoroethyl-substituted tripeptides, not only is antithrombin activity observed, but an inhibitor highly selective for thrombin versus other proteases, e.g. trypsin is obtained. This new class of compound may provide for a useful alternative or adjunct therapy to already known thrombin inhibitors and is useful in preventing coagulation of stored whole blood and in preventing coagulation in other biological samples for testing or storage.

SUMMARY OF THE INVENTION

The present invention relates to novel compounds of the formulae

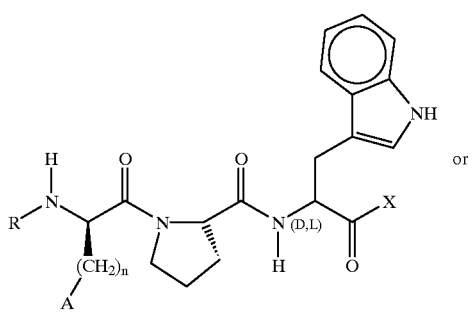

(I)

or

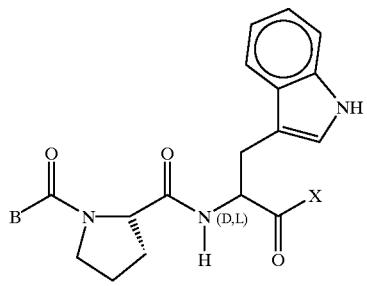

(IA)

wherein
A is phenyl or cyclohexyl;
B is a group of the formulae

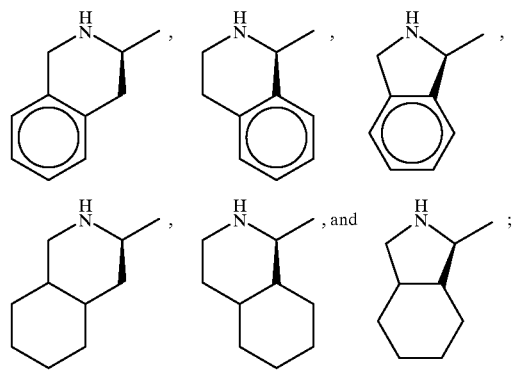

X is $-CF_3$, $-CF_2CF_3$, $-CF_2(CH_2)_tCH_3$, $-CF_2(CH_2)_tCOOR_1$, $-CF_2(CH_2)_tCONHR_1$, $-CF_2(CH_2)_tCH_2OR_1$ or $-CF_2(CH_2)_v CH=CH_2$;
R is H or $-CH_3$;
$R_1$ is H or $C_{1-6}$ alkyl;
n is zero or one;
t is the integer 2, 3 or 4;
v is the integer 1, 2 or 3;
or a stereoisomer or mixture thereof, a hydrate or a pharmaceutically acceptable salt thereof; and their use as thrombin inhibitors, useful in treating or preventing coronary artery and cerebrovascular disease, deep vein thrombosis, pulmonary embolism, stroke (thrombotic or embolic in origin), myocardial infarction, unstable or refractory angina, coronary thrombosis following angioplasty, restenosis, in preventing coagulation of stored whole blood and the like.

DETAILED DESCRIPTION OF THE INVENTION

As used in this application:
a) the designation "▶" refers to a bond that protrudes forward out of the plane of the page;
b) the designation "⫯⫯⫯" refers to a bond that protrudes backward out of the plane of the page;
c) the designation "∽" or the designation "(D,L)" refers to a bond for which the stereochemistry is not designated.

The term "$C_{1-6}$ alky" refers to a saturated hydrocarbyl radical of straight, brached or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like;

The term "stereoisomer" is a general term for all isomers that differ only in the orientation of their atoms in space. It includes mirror image isomers (enantiomers), geometric (cis/trans) isomers, and isomers of compounds with more than one chiral center that are not mirror images of one another (diastereomers).

The term "hydrate" means that the ketone of the compounds of the invention may exist as a dihydroxymethylene group.

The expression "pharmaceutically acceptable salt" is intended to apply to any non-toxic organic or inorganic salt of a compound of formulae (I) or (IA). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either the hydrated or substantially anhydrous form.

The following common abbreviations of the amino acids and amino and carboxy terminal groups, as put forth in Table 1, are used throughout this specification:

TABLE 1

| | |
|---|---|
| Gly (or G) - | glycine |
| Ala (or A) - | alanine |
| Val (or V) - | valine |
| Leu (or L) - | leucine |
| Ile (or I) - | isoleucine |
| Pro (or P) - | proline |
| Phe (or F) - | phenylalanine |
| Trp (or W) - | tryptophan |
| Ser (or S) - | serine |
| Met (or M) - | methionine |
| Thr (or T) - | threonine |
| Cys (or C) - | cysteine |
| Tyr (or Y) - | tyrosine |
| Gln (or Q) - | glutamine |
| Asn (or N) - | asparagine |
| Asp (or D) - | aspartic acid |
| Glu (or E) - | glutamic acid |
| Lys (or K) - | lysine |
| Arg (or R) - | arginine |
| His (or H) - | histidine |
| Cha - | cyclohexylalanine |
| Phg - | phenylglycine |
| Chg - | cyclohexylglycine |
| Tic - | tetrahydroisoquinoline carboxylic acid |
| Pip - | pipecolic acid |
| Orn - | ornithine |
| Boc - | tert-butyloxycarbonyl |
| Bzl - | benzyl |
| Cbz - | carbobenzyloxy |
| Ac - | acetyl |
| Suc - | succinyl |
| PAM - | phenylacetamidomethyl |

The natural amino acids, with the exception of glycine, contain a chiral carbon atom. Unless otherwise specifically indicated, the preferred compounds are the optically active amino acids of the L-configuration except, as indicated, it is preferred that the $P_3$ moiety, for example, the Phe, Cha, Phg or Chg moieties in Formula I, be in their D-configuration.

Regarding the compounds of Formulae I and IA, the $P_1$-α-amino acid residue (tryptophan) may be in its D- or L-configuration, or a mixture thereof, and the $P_2$-α-amino acid residue (proline) preferably is in its L-configuration. Similarly, the α-amino acid residue of the $P_3$ moiety (i.e., phenylalanine, cyclohexylalanine, etc.) is preferably in its D-configuration, with the preferred residues being Phe or Cha and the most preferred substituent being Phe. In the instance of the compounds of Formula IA, the $P_3$ moiety (substituent "B") is what is called a "TIC" derivative or a "TIC-like" derivative (the expression "TIC" being derived from tetrahydroisoquinoline carboxylic acid). In such instances, the bicyclic TIC-moiety formed with the $P_3$ nitrogen atom and the $P_3$-α-carbon are of the formulae

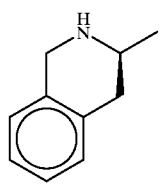

(2a)

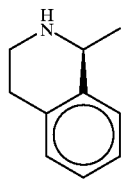

(2b)

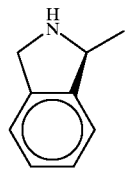

(2c)

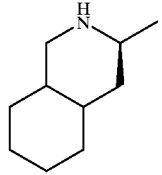

(2'a)

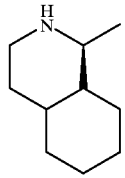

(2'b)

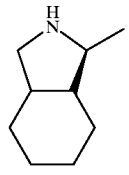

(2'c)

wherein (2a) and (2b) represent a 1,2,3,4-tetrahydroisoquinoline moiety, (2'a) and (2'b) represent a 1,2,3,4-decahydroisoquinoline moiety, and (2c) and (2'c) represent 2,3-dihydro-1H-isoindoyl and octahydro-1H- isoindolyl moieties, respectively. For convenience, the moieties hereinafter may also be referred to as "TIC-like modifications".

In general, the compounds of Formulae (I) and (IA) may be prepared using standard chemical reactions analogously known in the art. For example, compounds of Formula (I) wherein X is —CF$_2$CF$_3$ may be prepared as outlined in Scheme A. Starting materials, reagents, techniques, and procedures used in Scheme A are well known and appreciated by one of ordinary skill in the art.

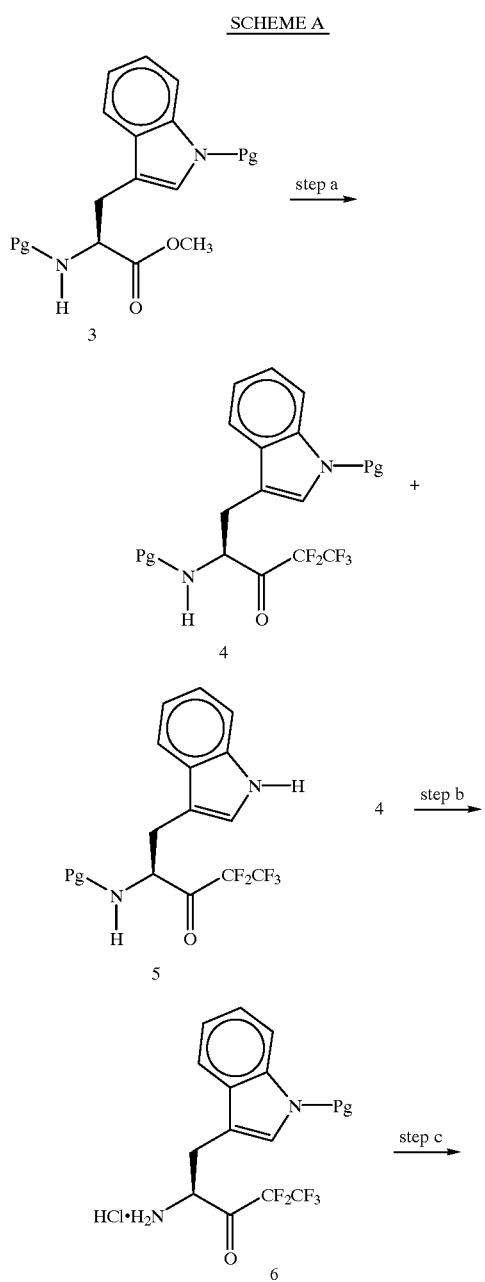

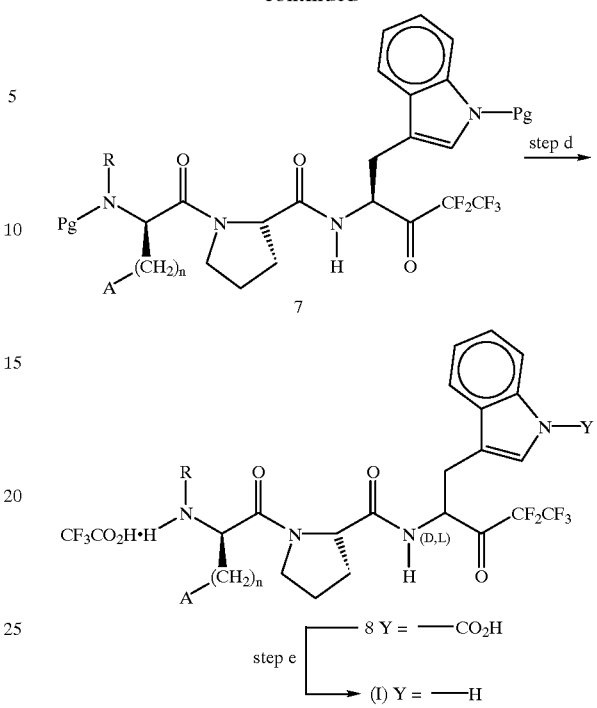

Scheme A provides a general synthetic procedure for preparing the compounds of Formula (I) wherein X is —CF$_2$CF$_3$, A and n are as previously defined and Pg is an N-protecting group which refers to a suitable protecting group including tert-butyloxycarbonyl (Boc), carbobenzyloxy (Cbz), tert-butyldimethylsilyl (TBDMS), tert-butyldiphenylsilyl (TBDPS) and the like, with tert-butyloxycarbonyl (Boc) being preferred.

In Scheme A, step a, the protected amino acid ester 3 is transformed into the protected pentafluoroethylketone 4 with the formation of byproduct 5. For example, the protected amino acid ester 3 is reacted with 3–6 molar equivalents of pentafluoroethyllithium, which may be generated in situ from pentafluoroethyl iodide and methyllithium.lithiumbromide complex as disclosed analogously by P. G. Gassman and N. J. O'Reilly, *J. Org. Chem.* 52, 2481–2490 (1987). This reaction can be conveniently carried out in a suitable anhydrous solvent such as diethyl ether or an anhydrous solvent mixture such as diethyl ether-toluene (9:1). The reaction is carried out at temperatures of from −30° C. to −80° C., with a temperature of from −50° C. to −65° C. being preferred. The protected pentafluoroethylketone 4 may be isolated from the reaction zone by extraction and evaporation, as is well known in the art. The product may be purified by techniques well known in the art, such as chromatography and recrystallization.

Alternatively, the protected pentafluoroethylketone 4 may be made by transforming a protected hydroxamate analog of 3 utilizing a reaction of the type described in M. R. Angelastro, J. P. Burkhart, P. Bey, N. P. Peet, *Tetrahedron Letters*, 33, 3265–3268 (1992).

In Scheme A, step b, the α-amine portion of the protected pentafluoroethylketone 4 is deprotected while the amino acid side chain functionality of 4 remains protected under conditions well known in the art as described by T. H. Green "Protection Groups in Organic Synthesis", John Wiley and Sons, Chapter 7 (1981), to provide the α-amine deprotected pentafluoroethylketone 6. For example, the bis-Boc-protected pentafluoroethylketone 4 can be contacted with a suitable acid, e.g. hydrogen chloride, in the presence of a suitable ethereal solvent such as dioxane and the like, to give the α-amine deprotected pentafluoroethylketone 6. The product 6 may be isolated and purified by techniques well known in the art.

In Scheme A, step c, the α-amine deprotected pentafluoroethylketone 6 is coupled with a compound of the formula:

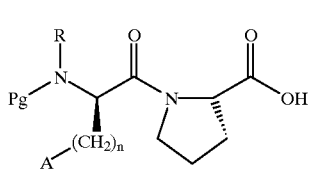

6a wherein all of the substituents are as previously defined, according to standard peptide coupling techniques. For example, in an ordinary peptide synthesis, peptides are elongated by deprotecting the α-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion or by condensation of fragments or a combination of both processes, or by solid phase peptide synthesis according to the method originally described by Merrifield, *J. Am. Cherm. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers form a bond which is stable to the elongation conditions but readily cleaved later. Examples of such carriers are: chloro- or bromomethyl resin, hydroxymethyl resin, and aminomethyl resin. Many of these resins are commercially available with the desired C-terminal amino acid already incorporated.

In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis", Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed using either solution (liquid phase) or solid phase techniques.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol.3, Academic Press, New York (1981), the disclosure of which is hereby incorporated by reference.

The α-carboxyl group of the C-terminal residue is usually protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid to be coupled to the growing peptide chain must be protected. Any protecting group known in the art can be used. Examples of these protecting groups include: 1) acyl types such as formyl, trifluoroacetyl, phthaloyl, and p-toluenesulfonyl; 2) aromatic carbamate types such as benzyloxycarbonyl (Cbz or Z) and substituted benzyloxycarbonyls, 1-(p-biphenyl)-1-methylethoxy-carbonyl, and 9-fluorenylmethyloxycarbonyl (Fmoc); 3) aliphatic carbamate types such as tert-butyloxycarbonyl (Boc), ethoxycarbonyl, diisopropyl-methoxycarbonyl, and allyloxycarbonyl; 4) cyclic alkyl carbamate types such as cyclopentyloxycarbonyl and adamantyloxycaronbyl; 5) alkyl types such as triphenylmethyl and benzyl; 6) trialkylsilanes such as trimethylsilane; and 7) thiol containing types such as phenylthiocarbonyl and dithiasuccinoyl. The preferred α-amino protecting group is either Boc, Cbz or Fmoc, preferably Boc. Many amino acid derivatives suitably protected for peptide synthesis are commercially available.

The α-amino group protecting group of the newly added amino acid residue is cleaved prior to the coupling of the next amino acid. Conditions for cleavage of such protecting groups are described in Greene, "Protective Groups in Organic Chemistry", Chapter 7, John Wiley & Sons, New York (1981). When the Boc group is used, the methods of choice are trifluoroacetic acid, neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that they must not be removed during the deprotection and coupling of the α-amino group.

For example, when Boc is used as the α-amino protecting group, a benzyl (Bn) ether can be used to protect the hydroxy containing side chains of amino acids such as Tyr, Ser or Thr.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

More specifically, in Scheme A, step c, a suitably protected dipeptide of structure 6a is dissolved in a suitable organic solvent under an inert atmosphere, such as nitrogen. Ethyl acetate is the preferred solvent for this coupling reaction. The solution is then treated with one to four equivalents of a suitable amine. Examples of suitable amines are tertiary organic amines such as tri-(lower alkyl)amines, for example, triethylamine; or aromatic amines such as picolines, collidines, and pyridine. When pyridines, picolines, or collidines are employed, they can be used in high excess and act therefore also as the reaction solvent. Particularly suitable for the coupling reaction is N-methylmorpholine (NMM). The solution is then cooled to about −20° C. and one equivalent of isobutyl chloroformate is added. The reaction is allowed to stir for about 10 to 30 minutes and 1 to 1.1 equivalents of the α-amine deprotected pentafluoroethylketone 6 is added to the reaction. The reaction is stirred for 30 minutes to 2 hours at about −20° C. and then it is allowed to warm to room temperature and stirred for 1 to 3 hours. The coupled product of structure 7 is then isolated and purified by techniques well known in the art, such as extractive techniques and flash chromatography. For example, the reaction is diluted with a suitable organic solvent such as methylene chloride, rinsed with water, dried over anhydrous magnesium sulfate, filtered and concentrated under vacuum. The residue is purified by flash chromatography on silica gel with a suitable eluent, such as ethyl acetate/hexane to provide the coupled product of structure 7.

In Scheme A, step d, the α-amine protecting group (Pg) and the protecting group on the $P_1$ amino acid side chain functionality (Pg) on the coupled product 7 are removed under conditions well known in the art, as described by T. W. Green, "Protective Groups in Organic Synthesis", Chapter 7, 1981, John Wiley & Sons, Inc., to provide the deprotected tripeptide 8. For example, when both Pg's are a tert-butyl carbamate (BOC) on the coupled product 7, the compound is dissolved in trifluoroacetic acid, stirred for several minutes and then concentrated under vacuum. The residue is then dissolved in $Et_2O$ and precipitated with hexane to provide the deprotected tripeptide 8.

Methodologies for the deprotection of tryptophan compounds are well known in the art, as described by Franzèn et al., *J. Chem. Soc.*, 1699–1700 (1984).

In Scheme A, step e, the deprotected tripeptide 8 undergoes a decarboxylation reaction to give a compound of Formula (I). For example, the deprotected tripeptide 8 is dissolved in a suitable chlorinated hydrocarbon solvent such as carbon tetrachloride, ethylene chloride, methylene chloride, chloroform, 1,2,4-trichlorobenzene, or o-dichlorobenzene and stirred for a period of time sufficient to complete the decarboxylation, e.g. from 24 to 72 hours. The product (I) can be isolated by techniques well known in the art.

Furthermore, the compounds of the invention wherein X is X', wherein X' is —$CF_3$, —$CF_2CF_3$, —$CF_2(CH_2)_tCH_3$, —$CF_2(CH_2)_tC(O)NHR$, —$CF_2(CH_2)_tCH_2OR$ or —$CF_2(CH_2)_vCH=CH_2$ may be prepared by procedures analogously known in the art, as disclosed in U.S. Pat. No. 5,391,705, issued Feb. 21, 1995. In essence, the synthesis of the fluorinated alkyl tripeptides of Formulae (I) and (IA) relies on a modified Dakin-West reaction of a 2-phenyl-5 (4H)-oxazolone and the anhydrides or acyl halides of trifluoroacetic acid, pentafluoropropionic acid or difluoropentenoic acid (depending on the desired X' moiety), to yield the requisited polyfluoro alkyl ketone amino acid derivatives for use as key intermediates. Further reactions then allow for the conversion of these amino acid analogs to the desired peptides of Formulae (I) and (IA). A general synthetic procedure for preparing the compounds of the invention wherein X is —$CF_3$, —$CF_2CF_3$, —$CF_2(CH_2)_tCH_3$, —$CF_2(CH_2)_tC(O)NHR$, —$CF_2(CH_2)_tCH_2OR$ or —$CF_2(CH_2)_vCH=CH_2$ is set forth in Scheme B. In Scheme B, starting materials and reagents unless indicated elsewhere in this application are well known and appreciated by one of ordinary skill in the art.

SCHEME B

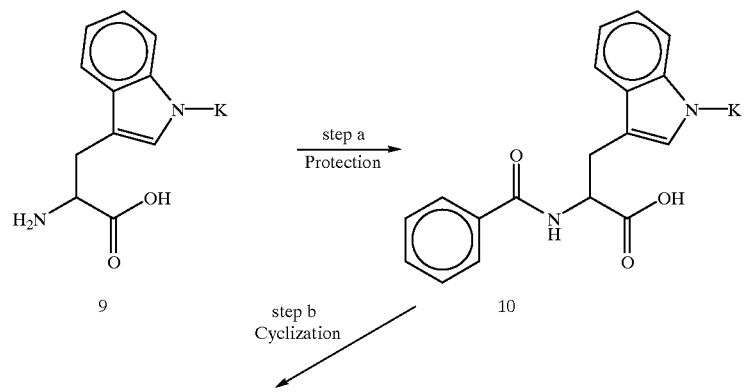

-continued
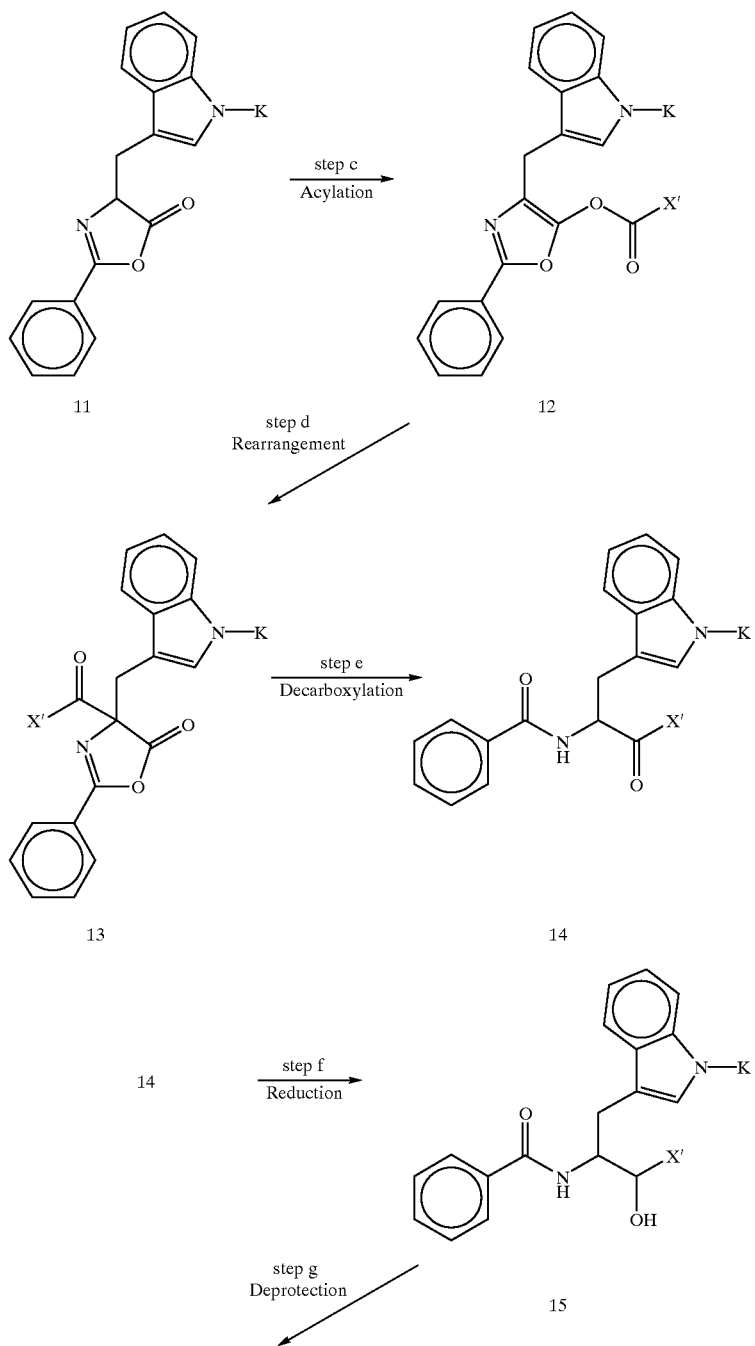

-continued
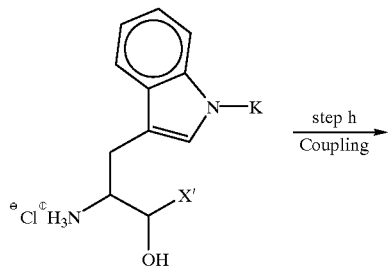
16
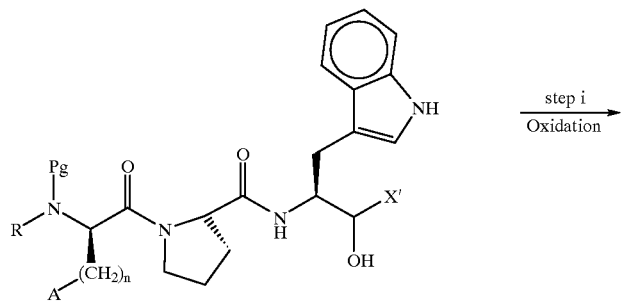
17
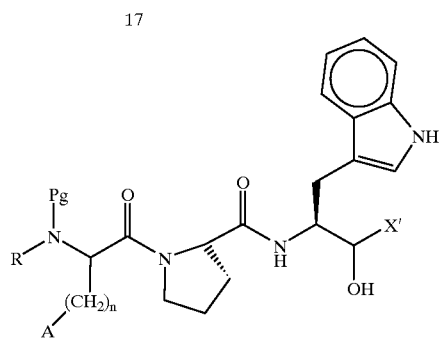
18
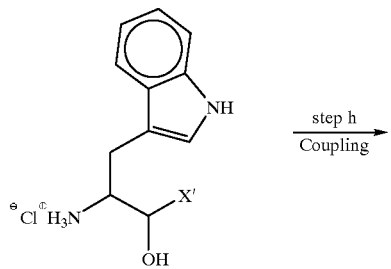
16

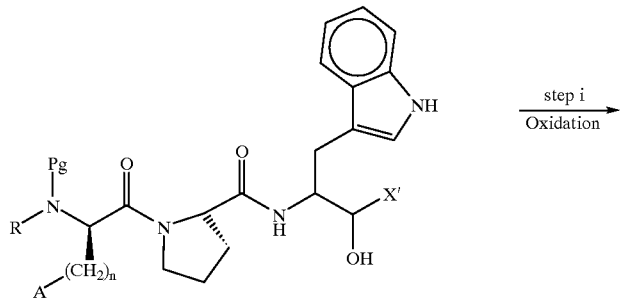

17

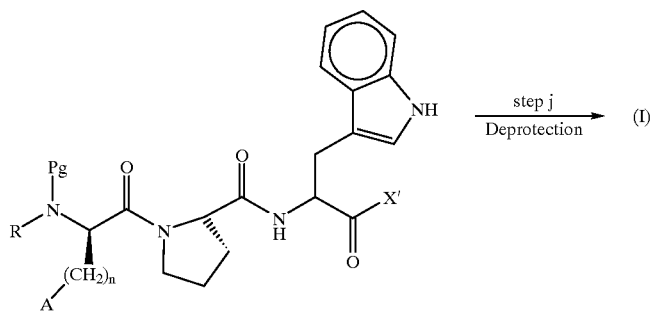

18

Scheme B provides a general synthetic procedure for preparing the compounds of the invention when X' is —$CF_3$, —$CF_2CF_3$, —$CF_2(CH_2)_tCH_3$, —$CF_2(CH_2)_tC(O)NHR_1$, —$CF_2(CH_2)_tCH_2OR_1$ or —$CF_2(CH_2)_vCH=CH_2$. All of the substituents disclosed in Scheme B are as previously defined unless otherwise indicated.

In Scheme B, step a, δ-K-tryptophan 9 is $N^\alpha$-protected according to standard N-protecting techniques well-known and appreciated by one skilled in the art to provide $N^\alpha$-K-$N^\delta$-benzyloxycarbonyl-tryptophan 10, wherein K refers to a suitable protecting group including carbobenzyloxy (Cbz), tert-butyldimethylsilyl (TBDMS), tert-butyldiphenylsilyl (TBDPS) and the like, with carbobenzyloxy (Cbz) being preferred.

For example, δ-Cbz-L-tryptophan 9 is $N^\alpha$-protected using benzoyl chloride and standard Schotten-Baumann conditions. Specifically, a solution of benzoyl chloride in an ethereal solvent, such as diethyl ether, is added concomitantly with sodium hydroxide to a solution of δ-Cbz-L-tryptophan 9 in sodium hydroxide, over a period of from about 0.5 to 1 hours, while maintaining the reaction temperature between 0° C. to about 5° C. The reaction mixture is then stirred for approximately 4 hours at room temperature, extracted with an ethereal solvent such as diethyl ether and acidified to about pH 1 using concentrated hydrochloric acid solution. Additional water is then added and the mixture is allowed to stand for approximately 48 hours. The solids are collected and purified by techniques well known to one skilled in the art to provide $N^\alpha$-benzoyl-$N^\delta$-benzyloxycarbonyltryptophan 10.

In Scheme B, step b, $N^\alpha$-benzoyl-$N^\delta$-benzyloxycarbonyltryptophan 10 is cyclized to provide the 2-phenyl-5-(4H)-oxazolone 11.

For example, a slurry of $N^\alpha$-benzoyl-$N^\delta$-benzyloxycarbonyltryptophan 10 in a suitable organic solvent, such as methylene chloride, is contacted with about 0.1 to 1.0 molar equivalents of dicyclohexylcarbodiimide. The reaction mixture is then stirred for about 2 to 5 hours and the resulting precipitated dicyclohexylurea by-product is filtered and washed with a suitable organic solvent, such as methylene chloride. The filtrate is then concentrated and diluted with a suitable ethereal solvent, such as diethyl ether and the process is optionally repeated. The cyclized product, 2-phenyl-5-(4H)-oxazolone 11, is then isolated and purified by techniques well known to one skilled in the art such as precipitation and crystallization.

In Scheme B, step c, 2-phenyl-5-(4H)-oxazolone 11 is acylated according to standard acylation techniques to provide the corresponding O-acyl compound of structure 12.

For example, a suitable tertiary amine, such as triethylamine, is added to a solution of the 2-phenyl-5-(4H)-oxazolone 11 in a suitable organic solvent, such as tetrahydrofuran or tetrahydrofuran/heptane mixtures, at a temperature range of from about −10° C. to about 10° C. under an inert atmosphere, preferably nitrogen. A solution of an appropriate acyl halide, or the corresponding appropriate anhydride, such as α,α-difluoropentenoyl chloride, trifluoroacetic anhydride, pentafluoropropionic anhydride, and the like, in a suitable organic solvent, such as heptane, is slowly added to the reaction mixture while maintaining the reaction temperature between about −10° C. and 10° C. After about 30 to 60 minutes, the reaction mixture is allowed to warm to room temperature and stirred for about another 30 minutes. The triethylamine hydrochloride salt is removed by extractive techniques well known in the art, such as filtration, and the filtrate is concentrated to give the corresponding O-acyl compound of structure 12.

In Scheme B, step d, the corresponding O-acyl compound of structure 12 is optionally reacted with an acylation catalyst to provide the corresponding C-acyl compound of structure 13.

For example, the corresponding O-acyl compound of structure 12 is dissolved in a suitable organic solvent, such as tetrahydrofuran and contacted with an acylation catalyst, such as a dialkylaminopyridine, preferably 4-dimethylaminopyridine (DMAP). The reaction mixture is then stirred for about 2–4 hours at room temperature to produce the C-acyl compound of structure 13, which is used without further isolation or purification.

In Scheme B, step e, the C-acyl compound of structure 13, is decarboxylated with a decarboxylating agent such as oxalic acid, succinic acid, and the like, with oxalic acid being preferred, to provide the desired decarboxylated fluorinated compounds of structure 14 as mixtures of the ketones and their hydrated forms.

For example, a solution containing from 1 to 5 molar equivalents of dried oxalic acid in a suitable organic solvent, such as tetrahydrofuran is added to the reaction mixture from Scheme B, step d, containing the C-acyl compound of structure 13, and is left stirring for 16–32 hours. The reaction mixture is then concentrated and treated with a suitable acid, such as hydrochloric acid, and extracted with ethyl acetate. The layers are separated and the organic layer is washed with an appropriate base such as sodium carbonate, sodium bicarbonate or sodium hydroxide, optionally washed with brine, dried with a suitable drying agent such as magnesium sulfate and concentrated. The decarboxylated product 14 is then isolated and purified by techniques well known to one skilled in the art such as precipitation and crystallization.

In Scheme B, step f, the decarboxylated fluorinated product of structure 14, is contacted with an appropriate reducing agent to provide the alcohol of structure 15.

As is well known and appreciated in the art, this reduction will give a derivative that is a mixture of stereoisomers.

Appropriate reducing agents are well known in the art and include but are not limited to lithium tri-t-butyloxyaluminohydride, potassium borohydride, lithium tri-sec-butylborohydride, lithium borohydride, sodium borohydride, and lithium triethylborohydride with sodium borohydride being preferred.

For example, the decarboxylated fluorinated product of structure 14 is contacted with a molar excess of an appropriate reducing agent. The reaction is carried out in a suitable solvent. Suitable solvents for hydride reductions are well known in the art, such as toluene, diethyl ether, methyl t-butyl ether, tetrahydrofuran (THF) and tetrahydrofuran/ethanol mixtures. The reaction is carried out at a temperature in the range of from −78° C. to about 10° C. The reduced product, the alcohol of structure 15, may be isolated from the reaction zone by extraction and then purified by methods well known in the art, such as chromatography and recrystallization.

In Scheme B, step g, the alcohol of structure 15 is contacted with an appropriate deprotecting agent, such as concentrated hydrochloric acid, and heated to about 100° C.–110° C. to provide the deprotected alcohol of structure 16.

For example, a solution of the alcohol of structure 15 in 6N aqueous hydrochloric acid is heated to reflux (about 110° C.) for about 15 to 20 hours. The reaction mixture is then cooled and benzoic acid crystals are removed by filtration. The filtrate is extracted with diethyl ether and the layers separated. The aqueous layer is treated with activated carbon and heated. It is then filtered, concentrated and dried to provide the deprotected alcohol product of structure 16.

In the special instance wherein it is desired to prepare compounds wherein X is —$CF_2(CH_2)_2CH_3$, the acid anhydride or acyl halide reactants used to prepare compounds of structure 12 would bear the moiety —$CF_2CH_2CH=CH_2$. Accordingly, the alcohol of structure 15 would also bear the moiety —$CF_2CH_2CH=CH_2$ which can be contacted with an alkylene reducing agent prior to deprotection to provide the deprotected alcohol of structure 16. An appropriate alkylene reducing agent includes diborane, diisoalkyl borane, borane/tertiary amine complexes and hydrogen in the presence of a hydrogenation catalyst. The most preferred alkylene reducing, agent is hydrogen in the presence of a hydrogenation catalyst. Examples of hydrogenation catalysts include platinum, palladium, rhodium, ruthenium and nickel. Both the metals, as finely dispersed solids or adsorbed on inert supports such as carbon or alumina, and certain soluble complexes of these metals exhibit catalytic activity.

For example, alcohol of structure 15 wherein X is —$CF_2CH_2CH=CH_2$ is dissolved in a suitable alcohol, such as isopropanol and a Suitable acid such as hydrochloric acid. The solution is then treated with an alkylene reducing agent, such as palladium dihydroxide adsorbed on an inert carbon support, and shaken under hydrogen gas (40–60 psi) for about 20 to 30 hours. The reaction mixture is filtered and concentrated to yield a $N^\alpha$-benzoyl-difluoro alcohol, hydrochloride. The $N^\alpha$-benzoyl-difluoro alcohol, hydrochloride is then contacted with an appropriate deprotecting, agent, such as hydrochloric acid and heated to reflux. The reaction mixture is cooled to room temperature, filtered and the filtrate is extracted with diethyl ether and the layers separated. The aqueous layer is treated with activated carbon, heated, filtered and concentrated to provide the appropriate deprotected alcohol of structure 16.

In the special instance wherein $R_3$ is —$CF_2(CH_2)_tCH_3$ with t being the integers 3 or 4, the corresponding olefins (e.g. —$CF_2CH_2CH=CH—CH_3$ or $CF_2CH_2CH=CHCH_2CH_3$) would be reduced. For the preparation of these latter type olefins, the starting acyl halides or an hydrides can be prepared by the methods described by R. W. Lang et al., *Tetrahedron Letters*, 29, 3291 (1988).

In Scheme B, step h, the appropriate deprotected alcohol of structure 16 is coupled with a compound of 6a according to standard peptide coupling, techniques as set forth in Scheme A, step c above to provide the tripeptide alcohol of structure 17.

In Scheme B, step i, the tripeptide alcohol of structure 17 is reacted with an appropriate oxidizing agent to provide the N-terminal protected tripeptide of structure 18.

For example, an appropriate tripeptide alcohol of structure 17 is reacted with an appropriate oxidizing agent, such as the Dess-Martin periodinane, a chromic anhydride pyridine complex, pyridinium dichromate, or a dimethyl sulfoxide complex, such as DMSO-$(COCl)_2$ (Swern conditions), to provide the N-terminal protected tripeptide of structure 18 using standard oxidizing techniques well known and appreciated by those skilled in the art. Standard oxidizing techniques include procedures such as the Swern oxidation procedure, Synthesis, 165 (1981); use of the Dess-Martin periodinane, Dess Martin, *J. Org. Chem.* 48, 4155 (1983); and the Jones oxidation procedure (see U.S. Pat. No. 5,391, 705); with the Swern oxidation procedure being most preferred. For example, approximately 1.5 equivalents of oxalyl chloride is dissolved in a suitable anhydrous organic solvent, such as methylene chloride, and cooled to a temperature of from about −55° C. to about −78° C. To this solution is added from about 3 to about 8 equivalents of methyl sulfoxide dropwise, maintaining the temperature at about −55° C. or below. An equivalent of tripeptide alcohol of structure 17 is dissolved in a suitable amount of anhydrous organic solvent, such as methylene chloride, and added slowly to the reaction with stirring. After addition is complete the reaction is stirred approximately 30 minutes at a temperature of from about −55° C. to about −78° C., an excess of a suitable organic base, such as triethylamine or N-methylmorpholine, is added and the reaction is allowed to warm to room temperature. The oxidized product, the N-terminal protected tripeptide of structure 18 is then isolated and purified by techniques well known to one skilled in the art such as extractive techniques, precipitation, crystallization and chromatography.

In Scheme B, step j, the N-terminal protected tripeptide of structure 18 is deprotected according to the procedures set forth in Scheme B, step g, to provide the desired compound of Formula (I).

In the special instance wherein X is —$CF_2(CH_2)_tCOOR_1$, the procedure for preparing the necessary intermediates (corresponding to the compounds of structure 16 but wherein the desired X moiety is —$CF_2(CH_2)_tCOOR_1$), the reactions of Scheme C may be utilized.

steps h, i and j to provide the desired compound of Formula (I) wherein X is —$CF_2(CH_2)_tCOOR_1$.

Alternatively, mesylation, elimination and hydrogenation reactions may be effected on the compounds of structures 19 and 20 by standard and well-known procedures and techniques such as are described by Sham et al., *Biochem. and Biophys. Res. Comm.* 175, 914 (1991) and U.S. Pat. No. 5,391,705 to provide the intermediate of structure 22.

The (α,α-difluoropentenoyl chloride intermediate 12a, required for preparation of the O-acyl compound of structure 12, when X is —$CF_2(CH_2)_2CH_3$ can be obtained as illustrated in U.S. Pat. No. 5,391,705 and set forth in Scheme D. The reagents, starting materials and techniques used in this process are readily available to one of ordinary skill in the art.

SCHEME D

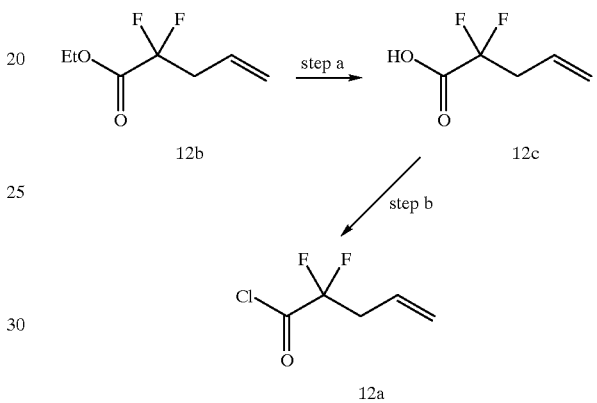

SCHEME C

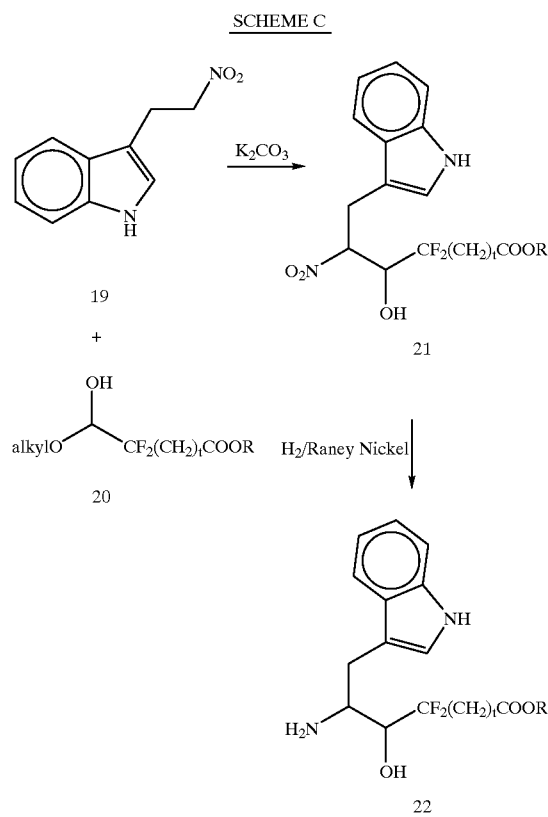

The intermediate 19 is disclosed by D. Ranganathan et al., *J. Chem. Res. Synop.*, 3, 78 (1983) and D. Ranganathan et al., *J. Org. Chem.* 45, 1185 (1980). The reactant 20 may be prepared by reacting bromodifluoroethyl acetate [see R. H. Abeles and C. P. Govardham, *Archives of Biochemistry and Biophysics*, 280, 137 (1990)] with the appropriate aldehyde, under Reformatsky conditions, to the corresponding difluoro alcohols. The difluoro alcohol 20 and the intermediate of structure 19 are then condensed with potassium carbonate in a suitable organic solvent, such as tetrahydrofuran, using techniques and conditions well know in the art to form the nitro alcohol intermediate of structure 21. The nitro alcohol intermediate of structure 21 is then reduced by catalytic hydrogenation to yield the intermediate of structure 22. The intermediate of structure 22, which is incorporated into structure 16, is then processed as described in Scheme B, In Scheme D, step a, 2,2-difluoro-4-pentenoic acid 12c, is prepared by hydrolysis of ethyl α,α-difluoropentenoate 12b (U.S. Pat. No. 5,391,705, issued Feb. 21, 1995) by techniques and procedures well known in the art, such as base hydrolysis.

For example, from about 1.0 to 1.5 molar equivalents of a suitable base, such as a lithium hydroxide, is added to a solution of ethyl α,α-difluoropentenoate 12b, also known as ethyl 2,2-difluoro-4-pentenoate (U.S. Pat No. 4,847,401, issued Jul. 11, 1989), in water at a temperature of from about −10° C. to about 10° C. The reaction mixture is allowed to warm to room temperature for about 2 to 4 hours and then heated at about 40° C. to about 55° C. for an additional 2 to 4 hours. Ethanol and water are removed from the reaction mixture and 2,2-difluoro-4-pentenoic acid 12c may be isolated from the reaction zone by extraction and then purified by methods well known in the art.

In Scheme D, step b, 2,2-difluoro-4-pentenoic acid 12c is contacted with a suitable chlorinating agent to yield 2,2-difluoro-4-pentenoyl chloride 12a.

An appropriate chlorinating agent is one that converts a hydroxyl group to a chloro group and does not cause the degradation of the starting material or the product. Appropriate chlorinating agents include phosphorous trichloride, thionyl chloride, oxalyl chloride and the like.

For example, 2,2-difluoro-4-pentenoic acid 12c is contacted with about 1.0 to 1.5 molar equivalents of an appropriate chlorinating agent. The reaction is carried out in a suitable solvent, such as dichloromethane, toluene or dimethylformamide. The reaction is carried out at a temperature of from about 20° C. to about 35° C. and generally requires about 4 to 24 hours. The product, 2,2-difluoro-4-pentenoyl chloride 12a, can be isolated by fractional distillation and purified by techniques well known in the art, such as chromatography.

For the preparation of compounds of Formula (IA), wherein X is —CF$_2$CF$_3$ and all of the remaining substituents are as previously defined, Scheme E may be used.

SCHEME E

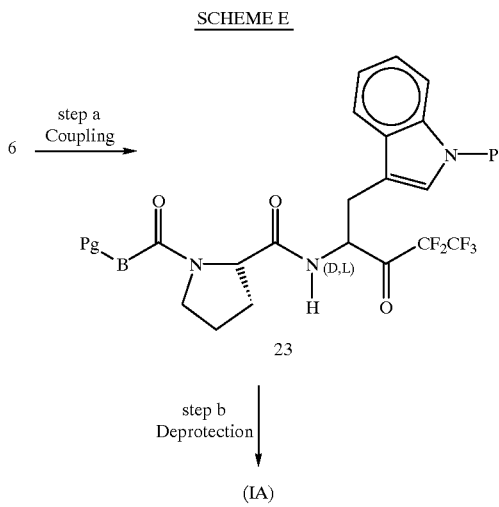

Scheme E provides a general synthetic procedure for preparing compounds of Formula (IA) wherein X is —CF$_2$CF$_3$ and all of the remaining substituents are as previously defined.

In Scheme E, step a, the α-amine deprotected pentafluoroethylketone 6 prepared in Scheme A is coupled with Pg-T-C(O)Pro-OH, wherein T is a TIC-like moiety as defined above and depicted as (2a), (2b), (2c), (2'a), (2'b) and (2'c) to form coupled product 23. The TIC-like moieties are disclosed in U.S. Pat. No. 5,391,705, issued Feb. 21, 1995, and Shuman et al., *J. Med. Chem.*, 36, 314–319 (1993), said patent and said reference being hereby incorporated by reference as if fully set forth. The coupling reaction is carried out in a manner directly analogous to the procedures described previously in Scheme A, step c.

In Scheme E, step b, the coupled product 23 is deprotected or cleaved from the solid phase under conditions well known in the art, such as that described previously in Scheme A, steps d and e to provide a tripeptide of Formula (IA).

For the preparation of compounds of Formula (IA), wherein all of the substituents are as previously defined, Scheme F may be used.

SCHEME F

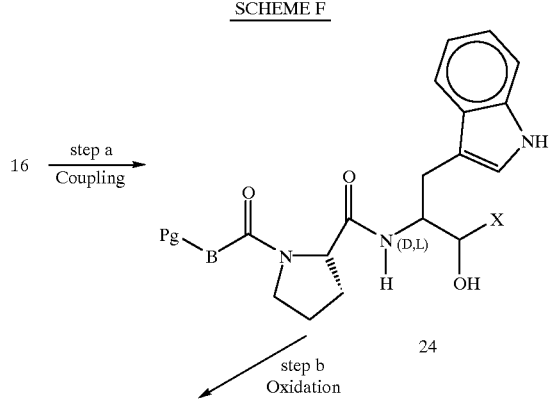

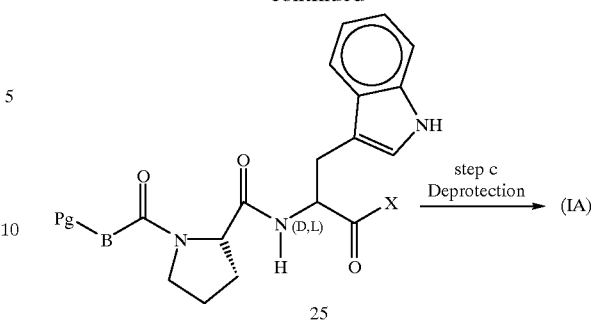

Scheme F provides for the preparation of compounds of Formula (IA), wherein all of the substituents are as previously defined.

In Scheme F, step a, the α-amine deprotected alcohol 16 prepared in Scheme B is coupled with-Pg-T-C(O)Pro-OH, wherein T is a TIC-like moiety as defined above and depicted as (2a), (2b), (2c), (2'a), (2'b) and (2'c) to form coupled product 24. The coupling reaction is carried out in a manner directly analogous to the procedures described previously in Scheme A, step c.

In Scheme F, step b, coupled product 24 is oxidized according to the procedures set forth in Scheme B, step i to provide the N-protected tripeptide of structure 25.

In Scheme F, step c, the N-protected tripeptide of structure 25 is deprotected according to the procedures set forth in Scheme B, step j to provide the desired compound of Formula (IA).

N-methylated α-amino acids can be prepared as described in Scheme G and generally in Pitzele, B. S. et al., *J. Med. Chem.*, 37, 888–896 (1994), herein incorporated by reference as if fully set forth. All of the substituents, unless otherwise indicated, are previously defined. The reagents and starting materials are readily available to one of ordinary skill in the art.

SCHEME G

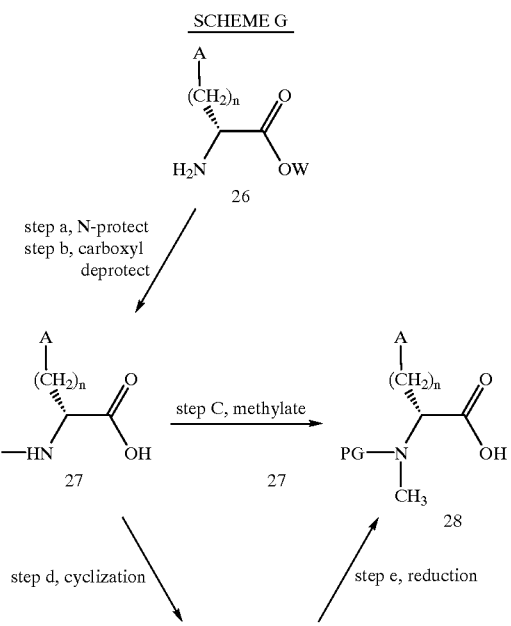

-continued

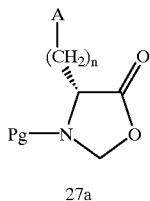

27a

In Scheme G, step a, an α-amino acid of structure 26 wherein W is a suitable α-carboxyl protecting group, such as a methyl ester or a solid phase resin, is coupled with Pg in a manner analogous to the procedures described in Scheme A, step c to provide the coupled product.

In Scheme G, step b, the coupled product is deprotected or cleaved from the solid phase under conditions well known in the art to provide the acid of structure 27. For example, wherein W is a methyl or ethyl group on structure 26, the compound is dissolved in a suitable organic solvent, such as ethanol and treated with approximately an equal volume of water. To this solution, with stirring is added 1 to 2 equivalents of lithium hydroxide and the reaction is allowed to stir for 1 to 6 hours. The resulting acid is then isolated and purified by techniques well known in the art. For example, the organic solvent is removed under vacuum and the remaining aqueous solution is acidified with dilute hydrochloric acid. The aqueous phase is then extracted with a suitable organic solvent, such ethyl acetate, and the combined organic extracts are dried over anhydrous magnesium sulfate, filtered and concentrated under vacuum. The residue can then be purified by flash chromatography on silica gel with a suitable eluent, such as methanol/chloroform to provide the acid of structure 27.

In Scheme G, step c, the acid 27 is N-methylated to provide the N-protected N-methylated compound of structure 28. For example, the acid 27 is dissolved in a suitable organic solvent, such as tetrahydrofuran, cooled to about 0° C. and treated with excess methyl iodide. Then 1 to 3 equivalents of sodium hydride is added to the solution which is stirred for about 10 minutes at 0° C. and then warmed to room temperature and stirred for 24 to 48 hours. The product is then isolated by techniques well known in the art, such as extractive methods. For example, dilute aqueous hydrochloric acid is added and the reaction is extracted with a suitable organic solvent, such as ethyl acetate. The organic extracts are then combined, washed with 5% sodium thiosulfate, brine, dried over anhydrous magnesium sulfate, filtered through a pad of silica gel and concentrated under vacuum to provide the N-protected, N-methylated compound 28.

Alternatively, the N-protected N-methylated compound 28 can be prepared following the procedure described in Scheme G, steps d and e, from the acid of structure 27.

In Scheme G, step d, the acid 27 is cyclized to provide the oxazolidine described by structure 27a. For example, the acid 27 is dissolved in a suitable organic solvent, such as benzene and treated with an excess of paraformaldehyde. To this is added about 0.2 to 0.4 equivalents of p-toluenesulfonic acid and the reaction is heated at reflux for about 23 hours with continuous removal of water using a Dean-Stark trap. The reaction is then allowed to cool to room temperature and the product is isolated and purified by techniques well known in the art. For example, the cooled reaction is concentrated under vacuum, the residue taken up in a suitable organic solvent, such as ethyl acetate, rinsed with saturated sodium bicarbonate, the organic phase dried over anhydrous magnesium sulfate, filtered and concentrated under vacuum. The residue is then purified by flash chromatography on silica gel with a suitable eluent, such as ethyl acetate/hexane to provide the oxazolidine 27a.

In Scheme G, step e, the oxazolidine 27a is reduced under conditions well known in the art to provide the N-protected N-methylated compound 28. For example, the oxazolidine 27a is dissolved in a suitable organic solvent, such as chloroform and treated with excess trifluoroacetic acid. To the solution is added an excess of triethylsilane with stirring at room temperature. The reaction is allowed to stir for 1 to 7 days and then concentrated under vacuum to provide the N-protected N-methylated compound 28.

The following examples present typical syntheses as described in Schemes A through G. These examples are understood to be illustrative only and are not intended to limit the scope of the present invention in any way. NMR spectra were recorded at 75 MHz for $^{13}C$, 282 MHz for $^{19}F$, and at 300 MHz for $^{1}H$; $^{19}F$ NMR signal are reported in ppm from $CFCl_3$. MS and HRMS data were recorded at 70 eV using computerized peak matching with perfluorokerosene as the HRMS reference. TLC analyses were performed with Merck DC-$F_{254}$ or Analtech GHLF silica gel plates, with visualization by alkaline permanganate and UV irradiation. Flash chromatography was performed with Merck silica gel 60 (0.040–0.063 mm). $CF_3CF_2Li$ was generated as described (Gassman & O'Reilly, *J. Org. Chem.*, 52, 2481–2490 (1987)) using $CF_3CF_2I$ obtained from Richmond Chemical Company. Deprotection of the tryptophan compounds utilized methodology analogous to that previously described (Franzèn et al., *J. Chem. Soc.*, 1699–1700 (1984)).

As used herein, the following terms have the indicated meanings: "g" refers to grams; "mmol" refers to millimoles; "mL" refers to milliliters; "bp" refers to boiling point; "mp" refers to melting point; "° C." refers to degrees Celsius; "mm Hg" refers to millimeters of mercury; "μL" refers to microliters; "μg" refers to micrograms; and "μM" refers to micromolar.

EXAMPLE 1

Preparation of 1H-Indole-1-carboxylic acid, 3-[2-[[(1,1-dimethoxy)carbonyl]amino]-4,4,5,5,5-pentafluoro-3-oxopenyl]-, 1,1-dimethylethyl ester, (S)-, (C); and Carbamic acid, [3,3,4,4,4-pentafluoro-1-(1H-indol-3-ylmethyl)-2-oxobutyl]-, 1,1-dimethylethyl ester, (S)-, (D).

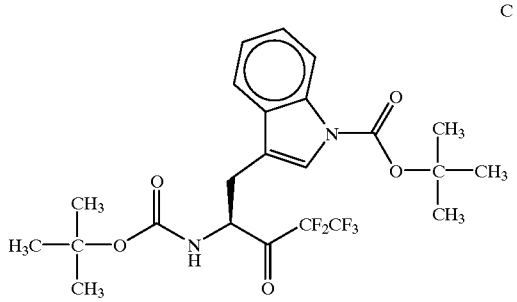

-continued

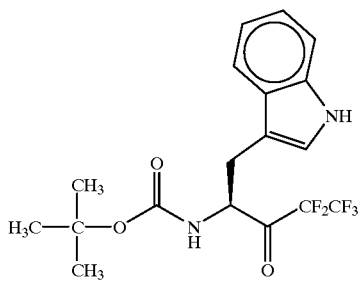

D

Scheme A, step a; To a stirred solution of Boc-Trp(Boc)-OCH$_3$ (Franzèn et al., *J. Chem. Soc.*, 1699–1700, 1984) (7.15 g, 17.08 mmol) in anhydrous Et$_2$O (60 mL) under a nitrogen atmosphere and cooled to −60° C. (internal thermometer) add condensed CF$_3$CF$_2$I (6.85 mL, 58.09 mmol). Add MeLi.LiBr (37.6 mL of a 1.5 M solution in Et$_2$O, 56.36 mmol) at a rate so as to maintain the internal reaction temperature between −52° C. and −62° C. After the addition is completed, stir the reaction mixture at −55° C. to −60° C. for 1 h. Quench the reaction by adding isopropanol (4.31 mL, 56.3 mmol) at a rate to maintain an internal reaction temperature of less than −55° C. Allow the reaction mixture to warm to −35° C. and then pour the reaction mixture into 10% aqueous KHSO$_4$ (100 mL). Separate the layers, wash the organic layer with 10% aqueous KHSO$_4$ (50 mL) and brine (25 mL) and dry with MgSO$_4$. Filter and concentrate to give the crude products C and D. Flash chromatography (7.5×19 cm silica gel column) eluting with a gradient (15 to 25%) of EtOAc in hexane gives C (5.43 g, 63%) as a yellow foam and D (1.50 g, 22%) as a pale yellow solid.

For compound C: TLC R$_f$0.37 (25:75 EtOAc:hexane); $^1$H NMR (CDCl$_3$, 3 days, ketone only, major rotamer) δ8.14 (br d, 1H, J=7.9 Hz, H$_7$), 7.50 (ddd, 1H, J=0.8, 1.1, 7.8 Hz, H$_4$), 7.42 (br s, 1H, H$_2$), 7.35 (ddd, J=1.3, 7.4, 8.4 Hz, H$_6$), 7.27 (dt, J=1.0, 7.8 Hz, H$_5$), 5.15–5.05 (m, 1H, CH), 4.99 (br d, 1H, J=7.6 Hz, NH), 3.36 (dd, 1H, 4.7, 15.0 Hz, ½ CH$_2$), 3.04 (dd, 1H, J=7.5, 15.0 Hz, ½ CH$_2$), 1.67 (s, 9H, N$^{in}$-Boc), 1.38 (s, 9H, Boc); $^{19}$F NMR (CDCl$_3$, 3 days, ketone only, major rotamer) δ−82.06 (s, CF$_3$), −120.85 and −122.48 (pr d, J=297 Hz, CF$_2$); MS (CI, NH$_3$) m/z (rel intensity) 524 (100, M+NH$_4^+$), 507 (3, M+), 468 (30), 412 (17), 230 (32), 130 (54). Anal. (C$_{23}$H$_{27}$F$_5$N$_2$O$_5$·0.34 H$_2$O) C,H,N.

For compound D: mp=135–141° C.; TLC R$_f$0.15 (25:75 EtOAc:hexane); $^1$H NMR (DMSO-d$_6$+D$_2$O, only hydrate species present) δ7.44–7.50 (m, 1H), 7.32–7.26 (m, 1H), 7.06–6.90 (m, 3H), 4.15–4.08 (m, 0.3H, CH of rotamer A), 3.98–3.91 (m, 0.7H, CH of rotamer B), 3.16 (dd, 0.3H, J=1.8, 14.2 Hz, ½ CH$_2$ of rotamer A), 3.12 (dd, 0.7H, J=1.6, 14.5 Hz, ½ CH$_2$ of rotamer B), 2.75 (dd, 0.7H, J=11.7, 14.6 Hz, ½ CH$_2$ of rotamer B), 2.58 (dd, 0.3H, J=11.9, 14.2 Hz, ½ CH$_2$ of rotamer A), 1.10 (s, 6.3H, Boc of rotamer B), 0.67 (s, 2.7H, Boc of rotamer A); $^{19}$F NMR (DMSO-d$_6$+D$_2$O, only hydrate species present) δ−77.54 (s, CF$_3$ of rotamer B), −77.63 (s, CF$_3$ of rotamer A), −121.46 and −123.59 (pr d, J=276 Hz, CF$_2$ of rotamer B), −121.46 and −123.35 (pr d, J=276 Hz, CF$_2$ of rotamer A); MS (CI, NH$_3$) m/z (rel intensity) 424 (37, M+NH$_4^+$), 368(100), 130(40); Anal. (C$_{18}$H$_{19}$F$_5$N$_2$O$_3$·0.34H$_2$O) C,H,N.

EXAMPLE 2

Preparation of 1H-Indole-1-carboxylic acid, 3-(2-amino-4,4,5,5,5-pentafluoro-3-oxopentyl)-, 1,1-dimethylethyl ester, monohydrochloride, (S)-.

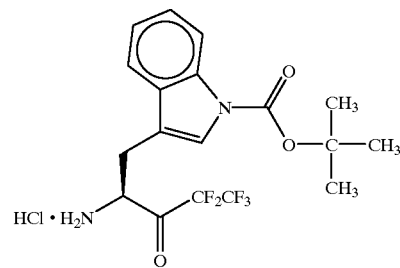

Scheme A, step b; Slowly add 4.0 N hydrogen chloride in dioxane (5.0 mL) to a stirred solution of compound C from example 1 (1.04 g, 2.00 mmol) in dioxane (2.4 mL) under a nitrogen atmosphere. After 1 h, suction filter the resultant suspension and wash the collected solid with Et$_2$O (3×10 mL). Dry the off-white solid under high vacuum over KOH pellets to provide 195 mg (22%) of the title compound as a mixture of ketone and hydrate (ratio 2:3). Because of the instability of the title compound, use the title compound immediately in the next step. Dilution of the combined filtrates from above and refrigeration provides additional title compound (571 mg, 64%).

$^1$H NMR (CDCl$_3$) δ8.79 (br s), 7.99 (br d, 1H, J=6.6 Hz), 7.88–7.66 (m), 7.51 (d, 0.4H, J=7.4 Hz, Ar—H of ketone), 7.41 (d, 0.6H, J=7.4 Hz, Ar—H of hydrate), 7.28–7.12 (m, 2H), 6.48 (br s, hydrate OH), 5.10–4.96 (m, 0.4H, CH of ketone), 3.75–3.93 (m, 0.6H, CH of ketone), 3.63–3.10 (m, 2H, CH$_2$), 1.55 (s, 9H, Boc); $^{19}$F NMR (CDCl$_3$) δ−79.48 (s, CF$_3$ of hydrate), −81.77 (s, CF$_3$ of ketone), −119.56 and −122.40 (pr d, J=297 Hz, CF$_2$ of ketone), −123.38 (br s, CF$_2$ of hydrate); MS (CI, NH$_3$) m/z (rel intensity) 424 (21, M+NH$_4^+$), 407 (42, MH+), 387 (100).

EXAMPLE 3

Preparation of L-Prolinamide, N-[(1,1-dimethylethoxy) carbonyl]-N-methyl-D-phenylalanyl-N-[1-[[1-[(1,1-dimethylethoxy)carbonyl]-1H-indol-3-yl]methyl]-3,3,4,4,4-pentafluoro-2-oxobutyl]-, (S)-.

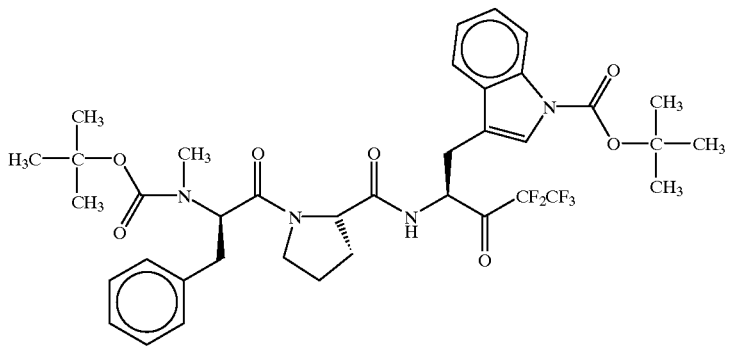

Scheme A, step c; To a stirred solution of N-Boc-N-methyl-D-Phe-L-Pro-OH (Veber et al., PCT Patent Application Publication No. WO 94/25051, published Nov. 10, 1994) (0.15 g, 0.41 mmol) in EtOAc (3 mL) under a nitrogen atmosphere and cooled to −18° C. is added N-methylmorpholine (45 μL, 0.41 mmol) followed by isobutyl chloroformate (53 μL, 0.41 mmol). After 15 min, add additional N-methylmorpholine (45 μL, 0.41 mmol) followed by the product of example 2 (0.18 g, 0.41 mmol). Stir the reaction mixture at −15 to −20° C. for 4 h, dilute with EtOAc (50 mL) and wash with 10% aqueous citric acid (2×25 mL), half-saturated aqueous NaHCO$_3$ (2×15 mL) and brine (25 mL). Drying (MgSO$_4$) followed by filtration and concentration gives crude product. Flash chromatography (2.5×12 cm silica gel column) eluting with EtOAc-hexane (45:55) gives the title compound (0.16 g, 52%, mixture of ketone and hydrate) as a pale yellow foam.

TLC R$_f$0.34 (45:55 EtOAc:hexane); $^{19}$F NMR (CDCl$_3$) δ−79.27 (s, CF$_3$ of hydrate), −82.09 (s, CF$_3$ of ketone), −122.81 and −124.74 (pr d, J=275 Hz, CF$_2$ of hydrate), −121.75 to −121.90 (m, CF$_2$ of ketone), ratio of ketone:hydrate~2:3; MS (CI, NH$_3$) m/z (rel intensity) 782 (30, M+NH$_4$$^+$), 765 (45, MH+), 205 (92), 122 (100); HRMS C$_{38}$H$_{46}$F$_5$N$_4$O$_7$ (MH+) calcd 765.3287, obsd 765.3281.

EXAMPLE 4
Preparation of L-Prolinamide, N-methyl-D-phenyialanyl-N-[1-[(1-carboxy-1H-indol-3-yl)methyl]-3,3,4,4,4-pentafluoro-2-oxobutyl]-, (S)-, mono(trifluoroacetate)

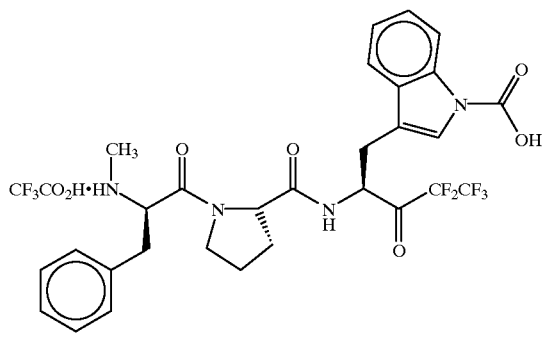

Scheme A, step d; To the product of example 3 (150 mg, 0.2 mmol) under a nitrogen atmosphere, add CF$_3$CO$_2$H (2 mL) and stir the resultant solution for 3 min. Remove the solvent, dissolve the residue in Et$_2$O (3 mL) and add hexane (20 mL) slowly with swirling. Suction filtration, under a nitrogen atmosphere, provides the title compound (117 mg, 82%) as an off-white solid. The title compound is unstable to decarboxylation.

$^1$H NMR (CDCl$_3$, NCH$_3$ signal only) δ2.44 (s, 3H, NCH$_3$); $^{19}$F NMR (CDCl$_3$) δ−82.11 (s, CF$_3$ of ketone), −121.60 to −122.91 (m, CF$_2$ of ketone); MS (FAB, MNBA) m/z (rel intensity) 609.2 (MH+, 46), 565.2 (MH—CO$_2$$^+$, 81), 448.2 (6), 404.2 (38), 134.1 (100).

EXAMPLE 5
Preparation of L-Prolinamide, N-methyl-D-phenylalanyl-N-[3,3,4,4,4-pentafluoro-1-(1H-indol-3-ylmethyl)-2-oxobutyl]-, mono(trifluoroacetate).

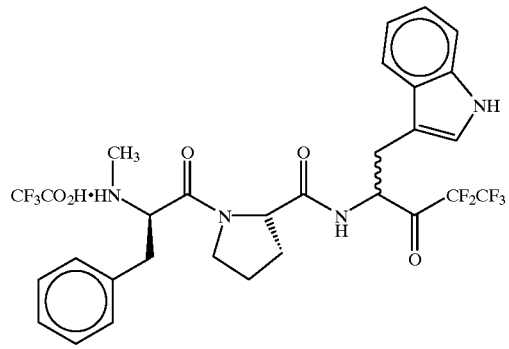

Scheme A, step e; Dissolve the product of example 4 (82 mg, 0.1 mmol) in CHCl$_3$ and stir for 48 h. Remove the solvent and dissolve the residue in CH$_2$Cl$_2$-hexane and then concentrate to give the title compound (76 mg, 100%, 1:1 mixture of DLL and DLD diastercomers) as a light yellow solid.

TLC R$_f$0.66 (5:95 Et$_3$N:CH$_3$CN); TLC R$_f$0.12 (5:95 Et$_3$N:EtOAc); $^1$H NMR (CDCl$_3$) δ9.69 (s, 0.5H, N$^{in}$-H of DLL diast.), 9.26 (s, 0.5H, N$^{in}$-H of DLD diast.), 8.18 (br d, 0.5H, J=6.4 Hz, DLD diast.), 7.61–7.02 (m), 5.11 (dd, 0.5H, J=5.8, 11.8 Hz, CH of Trp of DLD diast.), 5.04 (dt, 0.5H, J=3.6, 10.9 Hz, CH of Trp of DLL diast.), 4.54 (dd, 0.5H, J=2.0, 7.7 Hz, CH of Pro of DLD diast.), 4.42 (dd, 0.5H, J=1.9, 7.8 Hz, CH of Pro of DLL diast.), 4.03 (dd, 0.5H, J=4.2, 11.2 Hz, CH of Phe of DLD diast.), 3.97 (dd, 0.5H, J=4.4, 11.3 Hz, CH of Phe of DLL diast.), 3.5–2.9 (m), 2.23 (s, 1.5H, NCH$_3$ of DLD diast.), 2.10–1.90 (m), 1.93 (s, 1.5H, NCH$_3$ of DLL diast.), 1.70–1.65 (m), 1.50–1.22 (m); $^{19}$F NMR (CDCl$_3$) δ−82.11 (s, CF$_3$ of DLL diast.), −82.34 (s, CF$_3$ of DLD diast.), −120.22 and −123.54 (pr d, J=294 Hz, CF$_2$ of DLD diast.), −121.92 (s, CF$_2$ of DLL diast.), ratio of DLD to DLL=1:1; MS (CI, NH$_3$) m/z (rel intensity) 565 (MH+, 100), 547 (39), 436 (15), 276 (12), 259 (8); HRMS C$_{28}$H$_{30}$F$_5$N$_4$O$_3$ (MH+) calcd 565.2238, obsd 565.2253.

EXAMPLE 6

Preparation of 2-Pyrrolidinecarboxamide, N-[3,3,4,4,4-pentafluoro-1-(1H-indol-3-ylmethyl)-2-oxobutyl]-1-[(1,2,3,4-tetrahydro-3-isoquinolinyl)carbonyl]-, [2S-[1(S*), 2R*]]-, mono(trifluoroacetate).

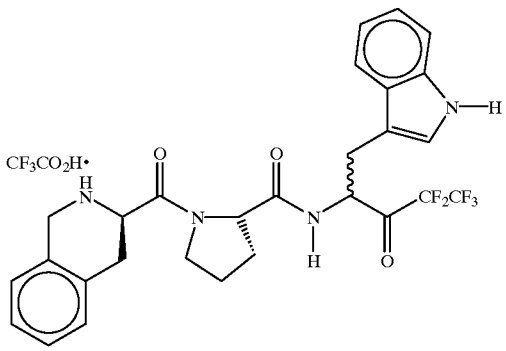

a) Preparation of Boc-D3-Tiq-Pro-Trp(Boc)—CF$_2$CF$_3$

Scheme E, step a; A stirred solution of Boc-D-3-Tiq-Pro-OH (Neises et al., U.S. Pat. No. 5,391,705, issued Feb. 21, 1995) (0.15 g, 0.41 mmol) in EtOAc (3 mL) under nitrogen atmosphere and cooled to −18° C. is contacted with N-methylmorpholine (45 µL, 0.41 mmol) followed by isobutyl chloroformate (53 µL, 0.41 mmol) and coupled to the product of example 2 (0.18 g, 0.41 mmol) in a manner analogous to that described in example 3, to provide the title compound.

b) Preparation of D-3-Tiq-Pro-Trp(COOH)—CF$_2$CF$_3$, mono(trifluoroacetate).

Scheme E, step b; The product of example 6 (a) (150 mg, 0.2 mmol) is deprotected in a manner analogous to that described in example 4 with CF$_3$CO$_2$H (2 mL), Et$_2$O (3 mL) and hexane (20 mL) to give the title compound.

c) Preparation of 2-Pyrrolidinecarboxamide, N-[3,3,4,4,4-pentafluoro-1-(1H-indol-3-ylmethyl)-2-oxobutyl]-1-[(1,2,3,4-tetrahydro-3-isoquinolinyl)carbonyl]-, [2S-[1(S*), 2R*]]-, mono(trifluoroacetate).

Scheme A, step e; The product of example 6(b) (82 mg, 0.1 mmol) is decarboxylated in a manner analogous to that described in example 5 with CHCl$_3$ (2 mL) and CH$_2$Cl$_2$-hexane to give the title compound.

EXAMPLE 7

Preparation of 2-Pyrrolidinecarboxamide, N-[3,3,4,4,4-pentafluoro-1-(1H-indol-3-ylmethyl)-2-oxobutyl]-1-[(1,2,3,4-tetrahydro-1-isoquinolinyl)carbonyl]-, [2S-[1(S*), 2R*]]-, mono(trifluoroacetate).

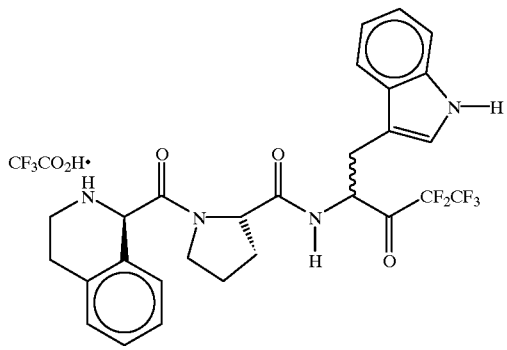

a) Preparation of Boc-D-1-Tiq-Pro-Trp(Boc)—CF$_2$CF$_3$

Scheme E, step a; A stirred solution of Boc-D-1-Tiq-Pro-OH (Neises et al., U.S. Pat. No. 5,391,705, issued Feb. 21, 1995) (0.15 g, 0.41 mmol) in EtOAc (3 mL) under nitrogen atmosphere and cooled to −18° C. is contacted with N-methylmorpholine (45 µL, 0.41 mmol) followed by isobutyl chloroformate (53 µL, 0.41 mmol) and coupled to the product of example 2 (0.18 g, 0.41 mmol) in a manner analogous to that described in example 3, to provide the title compound.

b) Preparation of D-1-Tiq-Pro-Trp(COOH)—CF$_2$CF$_3$, mono(trifluoroacetate).

Scheme E, step b; The product of example 7(a) (150 mg, 0.2 mmol) is deprotected in a manner analogous to that described in example 4 with CF$_3$CO$_2$H (2 mL), Et$_2$O (3 mL) and hexane (20 mL) to give the title compound.

c) Preparation of 2-Pyrrolidinecarboxamide, N-[3,3,4,4,4-pentafluoro-1-(1H-indol-3-ylmethyl)-2-oxobutyl]-1-[(1,2,3,4-tetrahydro-1-isoquinolinyl)carbonyl]-, [2S-[1(S*), 2R*]]-, mono(trifluoroacetate).

Scheme A, step e; The product of example 7(b) (82 mg, 0.1 mmol) is decarboxylated in a manner analogous to that described in example 5 with CHCl$_3$ (2 mL) and CH$_2$Cl$_2$-hexane to give the title compound.

EXAMPLE 8

Preparation of L-Prolinamide, 3-cyclohexyl-N-methyl-D-alanyl-N-[3,3,4,4,4-pentafluoro-1-(1H-indol-3-ylmethyl)-2-oxobutyl]-, mono(trifluoroacetate).

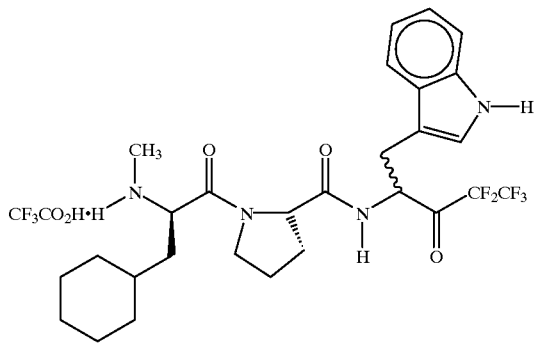

a) Preparation of N-Boc-N-methyl-D-Cha-OH

Scheme G, step c; Dissolve Boc-D-Cha-OH (10.8 g, 40 mmol,) in THF (200 mL) and cool the solution to 0° C. Add sodium hydride (4.8 g, 120 mmol, 60% dispersion in oil) in portions over a 1 hour period and stir for 20 minutes. Then add methyl iodide (19.7 mL, 316 mmol) and stir the reaction at 0° C. for 3 hours and at room temperature overnight.

Recool the reaction to 0° C. and slowly add water (100 mL). Concentrate to remove THF and wash the mixture with diethyl ether (2×150 mL). Acidify the aqueous layer with 6N HCl to approximately pH 3 and extract with ethyl acetate (4×100 mL). Combine the organic extracts, wash with 5% sodium thiosulfate (100 mL), brine (100 mL), dry over magnesium sulfate and concentrate under vacuum to provide the title compound.

b) Preparation of N-Boc-N-methyl-D-Cha-Pro-OCH$_3$

Scheme A, step c; Dissolve HCl·Pro-OCH$_3$ (0.33 g, 2.0 mmol) in DMF (20 mL) and cool the solution to 0° C. Add triethylamine (0.31 mL, 2.2 mmol) and stir for 10 minutes. Then add the product of example 8(a) (2.0 mmol, dissolved in 100 mL THF) followed by the addition of HOBt.1H$_2$O (0.27 g, 2.0 mmol) and EDC (0.40 g, 2.1 mmol). Stir the reaction at 0° C. for 3 hours and then at room temperature overnight. Concentrate the reaction under vacuum and take up the residue in 1N HCl (100 mL) and extract with ethyl acetate (3×100 mL). Combine the organic extracts, rinse with saturated sodium bicarbonate (100 mL), brine (100 mL), dry over anhydrous magnesium sulfate, pass through a short pad of silica gel and concentrate under vacuum. Purify the residue by flash chromatography to provide the title to product.

c) Preparation of N-Boc-N-methyl-D-Cha-Pro-OH

Scheme G, step b; Dissolve the product of example 8(b) (4.0 g, 10.2 mmol) in THF (100 mL) and water (50 mL). Add lithium hydroxide monohydrate (900 mg, 21.5 mmol) and stir the reaction at room temperature overnight. Concentrate to remove THF and then wash the residue with diethyl ether (2×100 mL) and acidify the aqueous layer with 6 N HCl to approximately pH 3. Then extract the acidified aqueous layer with ethyl acetate (3×100 mL). Combine the organic extracts, dry over anhydrous magnesium sulfate, and concentrate the filtrate under vacuum to provide the title acid.

d) Preparation of N-Boc-N-methyl-D-Cha-L-Pro-Trp(Boc)—CF$_2$CF$_3$

Scheme A, step c; A stirred solution of the product of example 8(c) (0.16 g, 0.41 mmol) in EtOAc (3 mL) under nitrogen atmosphere and cooled to −18° C. is contacted with N-methylmorpholine (45 μL, 0.41 mmol) followed by isobutyl chloroformate (53 μL, 0.41 mmol) and coupled to the product of example 2(0.18 g, 0.41 mmol) in a manner analogous to that described in example 3, to provide the title compound.

e) Preparation of N-methyl-D-Cha-L-Pro-Trp(COOH)—CF$_2$CF$_3$, mono(trifluoroacetate).

Scheme A, step d; The product of example 8(d)(154 mg, 2.0 mmol) is deprotected in a manner analogous to that described in example 4 with CF$_3$CO$_2$H (2 mL), Et$_2$O (3 mL) and hexane (20 mL) to give the title compound.

f) Preparation of L-Prolinamide, 3-cyclohexyl-N-methyl-D-alanyl-N-[3,3,4,4,4-pentafluoro-1-(1H-indol-3-ylmethyl)-2-oxobutyl]-, mono(trifluoroacetate).

Scheme A, step e; The product of example 8(e)(73 mg, 0.1 mmol) is decarboxylated in a manner analogous to that described in example 5 with CHCl$_3$ (2 mL) and CH$_2$Cl$_2$-hexane to give the title compound.

In further embodiments, the present invention provides a method for inhibiting thrombin in a patient in need thereof or in the treatment or prevention of a thrombin condition in a patient afflicted therewith comprising the administration thereto of a therapeutically effective amount of a compound of formulae (I) or (IA). The term "thrombin condition" refers to diseases or conditions characterized by thrombus or embolus formation and includes, but is not limited to coronary artery and cerebrovascular disease, deep vein thrombosis, pulmonary embolism, stroke (thrombotic or embolic in origin), myocardial infarction, unstable or refractory angina, coronary thrombosis following angioplasty, restenosis, and the like. Those experienced in this field are readily aware of the circumstances requiring thrombin inhibitors and/or anticoagulant therapy.

Compounds of formulae (I) and (IA) which are particularly preferred for the treatment of thrombin conditions include the compounds disclosed in Tables 5 and 6 below. Most preferred for the treatment of thrombin conditions is the compound L-Prolinamide, N-methyl-D-phenylalanyl-N-[3,3,4,4,4-pentafluoro-1-(1H-indol-3-ylmethyl)-2-oxobutyl]-, mono(trifluoroacetate).

As used herein, the term "patient" refers to a warm blooded animal such as a mammal and it is understood that guinea pigs, dogs, cats, rats, mice, horses, cattle, sheep, and humans are examples of mammals within the scope of the meaning of the term.

The term "therapeutically effective amount" refers to an amount which is effective, upon continuous infusion or upon single or multiple dose administration to the patient, in providing a reduction in the size of the thrombus or embolus or to a reduction in the extent of damage associated with thrombin conditions, leading to an improved outcome and/or a delay or prevention of disease progression as compared to outcomes expected in the absence of treatment. The term "therapeutically effective amount" does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formulae (I) or (IA) is expected to vary from about 25 milligram per kilogram of body weight per day (mg/kg/day) to about 200 mg/kg/day. Preferred amounts are expected to vary from about 40 to about 70 mg/kg/day. Intravenously, the most preferred doses will range from about 0.1 to about 20 mg/kg/minute during a constant rate infusion.

The compounds of this invention are selective inhibitors of thrombin. It is believed that the compounds of this invention exert their pharmacological effects through inhibition of the enzyme thrombin and thereby delay or prevent thrombin conditions including, coronary artery and cerebrovascular disease, deep vein thrombosis, pulmonary embolism, stroke (thrombotic or embolic in origin), myocardial infarction, unstable or refractory angina, coronary thrombosis following angioplasty, restenosis, and the like. However, it is understood that the present invention is not limited by any particular theory or proposed mechanism to explain its effectiveness in an end-use application.

In effecting treatment of a patient afflicted with a disease state described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, topically, and the like. Oral or intravenous administration is generally preferred. One skilled in the art of preparing formulations can readily select the proper form and mode of administration depending upon the particular characteristics of the compound selected for the disease state to be treated, the stage of the disease, and other relevant circumstances. Remington's Pharmaceutical Sciences, 18th Edition, Mack Publishing Co. (1990).

The compounds can be administered atone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formulae (I) or (IA) in admixture or otherwise in association with one or more inert carriers. These compositions are useful, for example, as assay standards, as convenient means of making bulk shipments, or whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

An anticoagulant amount of a compound of formulae (I) or (IA) is an amount which maintains the blood in its liquid state. Anticoagulant amounts of a compound of formulae (I) or (IA) will generally vary from about 45 $\mu$M to about 1,000 $\mu$M. Preferred anticoagulant amounts of a compound of formulae (I) or (IA) are from about 90 $\mu$M to about 300 $\mu$M. Inert carriers can be any material which does not degrade or otherwise covalently react with a compound of formulae (I) or (IA). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formulae (I) or (IA) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formulae (I) or (IA) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of a compound of formulae (I) or (IA) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

In Vitro Inhibitory Assays

The compounds of this invention are highly selective thrombin inhibitors versus other serine proteases such as trypsin. For example, the thrombin inhibitory activity of the compounds of Formulae (I) and (IA) can be demonstrated using the spectrophotometric assay according to the method of Tuppy et al., *Hoppe-Seyler's Z. Physiol. Chem.,* 329, p. 278 (1962), in which the liberation of p-nitroaniline is determined by measuring the increase in absorbance at 405 nm ($\epsilon=10800M^{-1}$ cm$^{-1}$). Thrombin is obtained from human plasma, available from Sigma Chemical Co. wherein the activity is expressed in NIH units. One vial contains 290 units (specific activity=3000 units per mg of protein) as a lyophilized powder which is reconstituted with 1 mL of water. The substrate is the chromophoric peptide, Sarcosyl-Proline-Arginine-p-nitroanilide ($K_m$=0.9 mM), the buffer is 0.1M Tris, pH 7.4 (final volume 1 mL) and the assay is carried out at a temperature of about 30° C. with 0.029 NIH units of enzyme required per assay. Kinetic characterization of immediate inhibitors is by means of the Dixon plot, whereas the characterization of slow- and/or tight-binding inhibitors uses data analysis techniques reviewed by Williams and Morrison. Kinetic characterization of time dependent inhibitors is by means of a Kitz & Wilson plot, Kitz R. and Wilson I. B., *J. Biol. Chem.,* 237, 3245–3249 (1962).

The trypsin inhibitory activity of the compounds of Formulae (I) and (IA) can be demonstrated using the spectrophotometric assay according to the method of Tuppy et al., *Hoppe-Seyler's Z. Physiol. Chem.,* 329, p. 278 (1962), immediately described above. Trypsin is obtained from porcine pancreas, available from Sigma Chemical Co. wherein the activity is expressed in Sigma units. The specific activity of the trypsin source is 15900 Sigma units per mg of protein where one unit is defined as the amount of enzyme that gives an increase in absorbance at 253 nm of 0.001 per min as the result of the hydrolysis of Benzoyl-Arginine-Ethylester, at pH 7.6 and 25° C. The substrate is the peptide Benzoyl-Arginine-p-nitroanilide ($K_M$=1.7 nM), the buffer is 0.05M Tris, 0.05M CaCl$_2$, pH 7.8 (final volume 1 mL) and the assay is carried out at a temperature of 30° C. with 8 Sigma units of enzyme required per assay. Kinetic characterization of immediate inhibitors is by means of the Dixon plot, whereas the characterization of slow- and/or tight-binding inhibitors uses data analysis techniques reviewed by Williams and Morrison. Kinetic characterization of time dependent inhibitors is by means of a Kitz & Wilson plot.

Table 2 summarizes the ability of a selected compound of the invention to selectively inhibit thrombin versus trypsin. As used herein, "TFA" refers to trifluoroacetic acid

TABLE 2

| Compound | Ki (nM) Thrombin | Ki (nM) Trypsin |
|---|---|---|
| TFA.HNMe-D-Phe-L-Pro-D,L-Trp-CF$_2$CF$_3$ | 450 | ~100,000 |

Determination of Anticoagulant Activity
Experimental Animals
Male Sprague-Dawley rats (200–450 gm) purchased from Harlan Sprague Dawley, Inc., (Indianapolis, Ind. 46229) were used in these studies.
Coagulation Assay
Activated partial thromboplastin time (aPTT) determinations are carried out using the reagents and methods of Dade Diagnostics, Inc. (Aguada, Puerto Rico 00602). All clotting times were measured semiautomatically using a MLA-Electra 750, MLA, Inc. (Pleasantville, N.Y. 10570). The concentration required for doubling the clotting time (ID$_2$) was calculated using simple linear regression. Table 3 illustrates the anticoagulant activity of a selected compound of this invention.

TABLE 3

| Compound | ID$_2$ ($\mu$M) |
|---|---|
| TFA.HNMe-D-Phe-L-Pro-D,L-Trp-CF$_2$CF$_3$ | 44.9 |

In Vivo Measurement of Activated Partial Thromboplastin Time (aPTT) In Rat Plasma Activated partial thromboplastin time (aPTT) measurements were made in rat plasma at various times after injecting the animals with TFA·HNMe-D-Phe-L-Pro-D,L-Trp—CF$_2$CF$_3$. Male Sprague-Dawley rats (200–450 g) purchased from Harlan Sprague Dawley, Inc., (Indianapolis, Ind. 46229) are used in these studies. Results from dosages of 5 mg/kg, i.v., 10 mg/kg, i.v., and 30 mg/kg, i.v. are disclosed in Table 4:

TABLE 4

The Effect of on TFA.HNMe-D-Phe-L-Pro-D,L-Trp-CF$_2$CF$_3$ on aPTT in Rats (n = 2)

| Dose (mg/kg) | Route* | aPTT@ (seconds) Time After Dosing (min.) | | | | |
|---|---|---|---|---|---|---|
| | | 0 min. | 5 min. | 15 min. | 30 min. | 60 min. |
| 5 | i.v. | 21.2 | 19.0 | 22.7 | 18.6 | 17.6 |
| 10 | i.v. | 18.8 | 17.4 | 18.0 | 15.7 | 12.6 |
| 30 | i.p. | 19.2 | 20.8 | 19.2 | 19.4 | 18.7 |

*i.v. = intravenous; i.p. = intraperitoneal. @aPTT = activated partial thromboplastin time.

The preferred compounds of this invention (I and IA) which are of particular interest are those compounds specified in Tables 5 and 6. Table 5 discloses the preferred compounds of Formula I.

TABLE 5

Compounds of Formula I

| R | A | n | X |
|---|---|---|---|
| —CH$_3$ | phenyl | one | —CH$_3$ |
| —CH$_3$ | phenyl | zero | —CH$_3$ |
| —CH$_3$ | cyclohexyl | one | —CH$_3$ |
| —CH$_3$ | cyclohexyl | zero | —CH$_3$ |
| —H | phenyl | one | —CH$_3$ |
| —H | phenyl | zero | —CH$_3$ |
| —H | cyclohexyl | one | —CH$_3$ |
| —H | cyclohexyl | zero | —CH$_3$ |
| —CH$_3$ | phenyl | one | —CF$_2$CF$_3$ |
| —CH$_3$ | phenyl | zero | —CF$_2$CF$_3$ |
| —CH$_3$ | cyclohexyl | one | —CF$_2$CF$_3$ |
| —CH$_3$ | cyclohexyl | zero | —CF$_2$CF$_3$ |
| —H | phenyl | one | —CF$_2$CF$_3$ |
| —H | phenyl | zero | —CF$_2$CF$_3$ |
| —H | cyclohexyl | one | —CF$_2$CF$_3$ |
| —H | cyclohexyl | zero | —CF$_2$CF$_3$ |
| —CH$_3$ | phenyl | one | —CF$_2$(CH$_2$)$_2$CH$_3$ |
| —CH$_3$ | phenyl | zero | —CF$_2$(CH$_2$)$_2$CH$_3$ |
| —CH$_3$ | cyclohexyl | one | —CF$_2$(CH$_2$)$_2$CH$_3$ |
| —CH$_3$ | cyclohexyl | zero | —CF$_2$(CH$_2$)$_2$CH$_3$ |
| —H | phenyl | one | —CF$_2$(CH$_2$)$_2$CH$_3$ |
| —H | phenyl | zero | —CF$_2$(CH$_2$)$_2$CH$_3$ |
| —H | cyclohexyl | one | —CF$_2$(CH$_2$)$_2$CH$_3$ |
| —H | cyclohexyl | zero | —CF$_2$(CH$_2$)$_2$CH$_3$ |
| —CH$_3$ | phenyl | one | —CF$_2$(CH$_2$)$_3$CH$_3$ |
| —CH$_3$ | phenyl | zero | —CF$_2$(CH$_2$)$_3$CH$_3$ |
| —CH$_3$ | cyclohexyl | one | —CF$_2$(CH$_2$)$_3$CH$_3$ |
| —CH$_3$ | phenyl | one | —CF$_2$(CH$_2$)$_4$CH$_3$ |
| —CH$_3$ | phenyl | one | —CF$_2$(CH$_2$)$_2$COOCH$_3$ |
| —CH$_3$ | cyclohexyl | one | —CF$_2$(CH$_2$)$_4$COOCH$_3$ |
| —H | phenyl | one | —CF$_2$(CH$_2$)$_2$COOEt |

TABLE 5-continued

Compounds of Formula I

| R | A | n | X |
|---|---|---|---|
| —CH$_3$ | phenyl | one | —CF$_2$(CH$_2$)$_2$COOEt |
| —CH$_3$ | phenyl | one | —CF$_2$(CH$_2$)$_2$CONHCH$_3$ |
| —CH$_3$ | cyclohexyl | one | —CF$_2$(CH$_2$)$_2$CONHCH$_3$ |
| —H | phenyl | zero | —CF$_2$(CH$_2$)$_2$CONHCH$_3$ |
| —CH$_3$ | phenyl | one | —CF$_2$(CH$_2$)$_2$CH$_2$OCH$_3$ |
| —H | phenyl | zero | —CF$_2$(CH$_2$)$_2$CH$_2$OCH$_3$ |
| —H | phenyl | one | —CF$_2$(CH$_2$)$_2$CH$_2$OCH$_3$ |
| —CH$_3$ | phenyl | one | —CF$_2$(CH$_2$)$_4$CH$_2$OCH$_3$ |
| —CH$_3$ | cyclohexyl | one | —CF$_2$(CH$_2$)$_4$CH$_2$OCH$_3$ |
| —CH$_3$ | phenyl | one | —CF$_2$(CH$_2$)$_1$CH═CH$_2$ |
| —H | phenyl | zero | —CF$_2$(CH$_2$)$_1$CH═CH$_2$ |
| —H | phenyl | one | —CF$_2$(CH$_2$)$_1$CH═CH$_2$ |
| —CH$_3$ | cyclohexyl | one | —CF$_2$(CH$_2$)$_1$CH═CH$_2$ |

Similarly, Table 6 discloses the preferred compounds of Formula IA.

TABLE 6

Compounds of Formula IA

| B | X |
|---|---|
| (2a) | —CF$_3$ |
| (2a) | —CF$_2$CF$_3$ |
| (2a) | —CF$_2$(CH$_2$)$_2$CH$_3$ |
| (2a) | —CF$_2$(CH$_2$)$_4$CH$_3$ |
| (2a) | —CF$_2$(CH$_2$)$_2$COOCH$_3$ |
| (2a) | —CF$_2$(CH$_2$)$_2$COOEt |
| (2a) | —CF$_2$(CH$_2$)$_2$CONHCH$_3$ |
| (2a) | —CF$_2$(CH$_2$)$_2$CH$_2$OCH$_3$ |
| (2a) | —CF$_2$(CH$_2$)$_1$CH═CH$_2$ |
| (2b) | —CF$_3$ |
| (2b) | —CF$_2$CF$_3$ |
| (2b) | —CF$_2$(CH$_2$)$_2$CH$_3$ |

TABLE 6-continued

Compounds of Formula IA

| B | X |
|---|---|
| (2b) | —CF$_2$(CH$_2$)$_4$CH$_3$ |
| (2b) | —CF$_2$(CH$_2$)$_2$COOCH$_3$ |
| (2b) | —CF$_2$(CH$_2$)$_2$COOEt |
| (2b) | —CF$_2$(CH$_2$)$_2$CONHCH$_3$ |
| (2b) | —CF$_2$(CH$_2$)$_2$CH$_2$OCH$_3$ |
| (2b) | —CF$_2$(CH$_2$)$_1$CH=CH$_2$ |
| (2c) | —CF$_3$ |
| (2c) | —CF$_2$CF$_3$ |
| (2c) | —CF$_2$(CH$_2$)$_2$CH$_3$ |
| (2c) | —CF$_2$(CH$_2$)$_2$COOCH$_3$ |
| (2c) | —CF$_2$(CH$_2$)$_2$COOEt |
| (2c) | —CF$_2$(CH$_2$)$_2$CONHCH$_3$ |
| (2c) | —CF$_2$(CH$_2$)$_2$CH$_2$OCH$_3$ |
| (2c) | —CF$_2$(CH$_2$)$_1$CH=CH$_2$ |
| (2′a) | —CF$_2$CF$_3$ |

TABLE 6-continued
Compounds of Formula IA
| B | X |
|---|---|
| 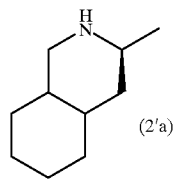 (2'a) | —$CF_2(CH_2)_2CH_3$ |
| 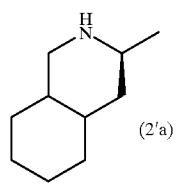 (2'a) | —$CF_2(CH_2)_2COOCH_3$ |
| 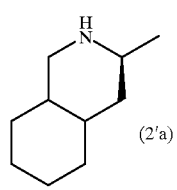 (2'a) | —$CF_2(CH_2)_2CONHCH_3$ |
| 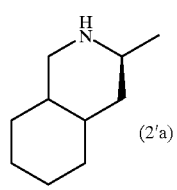 (2'a) | —$CF_2(CH_2)_2CH_2OCH_3$ |
| 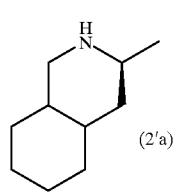 (2'a) | —$CF_2(CH_2)_1CH=CH_2$ |
| 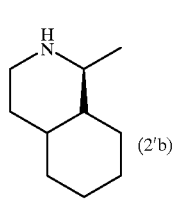 (2'b) | —$CF_3$ |
| 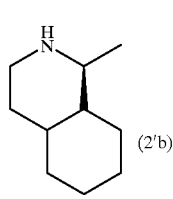 (2'b) | —$CF_2CF_3$ |
TABLE 6-continued
Compounds of Formula IA
| B | X |
|---|---|
| 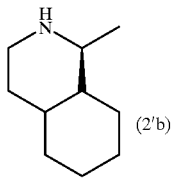 (2'b) | —$CF_2(CH_2)_2CH_3$ |
| 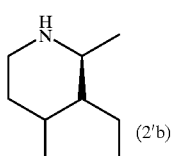 (2'b) | —$CF_2(CH_2)_2COOCH_3$ |
| 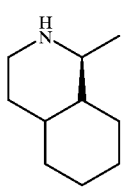 (2'b) | —$CF_2(CH_2)_2CONHCH_3$ |
| 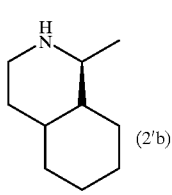 (2'b) | —$CF_2(CH_2)_2CH_2OCH_3$ |
| 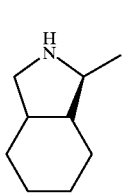 (2'c) | —$CF_3$ |
| 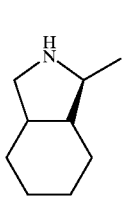 (2'c) | —$CF_2CF_3$ |
| 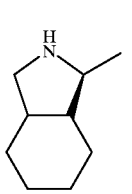 (2'c) | —$CF_2(CH_2)_2CH_3$ |

TABLE 6-continued

Compounds of Formula IA

| B | X |
|---|---|
| 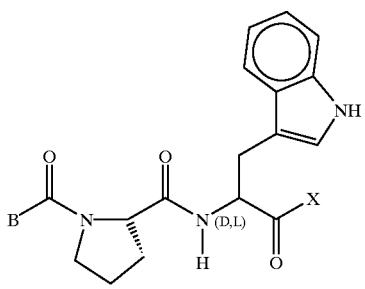 (2'c) | —CF$_2$(CH$_2$)$_2$COOCH$_3$ |
| (2'c) | —CF$_2$(CH$_2$)$_2$CONHCH$_3$ |
| (2'c) | —CF$_2$(CH$_2$)$_2$CH$_2$OCH$_3$ |

While the invention has been described in connection with specific embodiments thereof, it will be understood that it is capable of further modifications and this application is intended to cover any variations, uses, or adaptations of the invention following, in general, the principles of the invention and including such departures form the present disclosure as come within known or customary practice within the art to which the invention pertains and as may be applied to the essential features hereinbefore set forth, and as follows in the scope of the appended claims.

What is claimed is:

1. A compound of the formulae

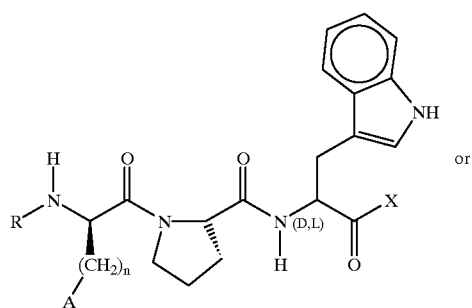

(I)

or

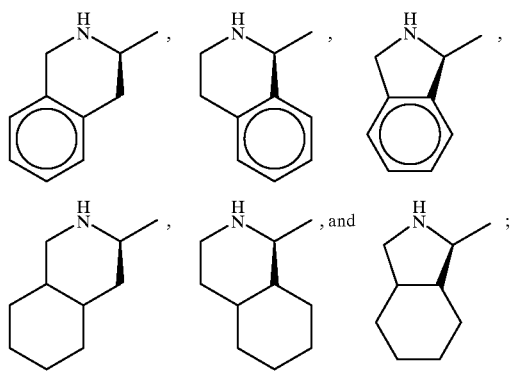

(IA)

wherein

A is phenyl or cyclohexyl;

B is a group of the formulae

X is —CF$_3$, —CF$_2$CF$_3$, —CF$_2$(CH$_2$)$_t$CH$_3$, —CF$_2$(CH$_2$)$_t$COOR$_1$, —CF$_2$(CH$_2$)$_t$CONHR$_1$, —CF$_2$(CH$_2$)$_t$CH$_2$OR$_1$ or —CF$_2$(CH$_2$)$_v$CH=CH$_2$;

R is H or —CH$_3$;

R$_1$ is H or C$_{1-6}$ alkyl;

n is zero or one;

t is the integer 2, 3 or 4;

v is the integer 1, 2 or 3;

or a stereoisomer or mixture thereof, a hydrate or a pharmaceutically acceptable salt thereof.

2. A compound of claim 1 wherein X is selected from the group consisting of —CF$_3$, —CF$_2$CF$_3$, —CF$_2$(CH$_2$)$_2$CH$_3$, —CF$_2$(CH$_2$)$_2$CO$_2$CH$_2$CH$_3$, —CF$_2$(CH$_2$)$_2$CONHCH$_3$ and —CF$_2$(CH$_2$)$_4$CONHCH$_3$.

3. A compound of claim 2 having the structure of Formula I wherein A is phenyl, n is one and R is —CH$_3$.

4. A compound of claim 2 having the structure of Formula I wherein A is cyclohexyl and n is one.

5. A compound of claim 1 having the structure of Formula IA wherein X is selected from the group consisting of —CF$_3$, —CF$_2$CF$_3$, —CF$_2$(CH$_2$)$_2$CH$_3$, —CF$_2$(CH$_2$)$_2$CO$_2$CH$_2$CH$_3$, —CF$_2$(CH$_2$)$_2$CONHCH$_3$ and —CF$_2$(CH$_2$)$_4$CONHCH$_3$.

6. A compound of claim 5 having the structure of Formula IA wherein B is

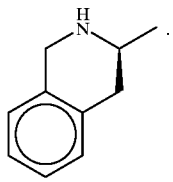

7. A compound of claim 5 having the structure of Formula IA wherein B is

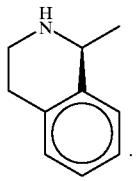

8. A compound of claim 3 wherein X is —CF$_2$(CH$_2$)$_2$CH$_3$.
9. A compound of claim 4 wherein X is —CF$_2$(CH$_2$)$_2$CH$_3$.
10. A compound of claim 5 wherein X is —CF$_2$(CH$_2$)$_2$CH$_3$.
11. A compound of claim 3 wherein X is —CF$_2$CF$_3$.
12. A compound of claim 4 wherein X is —CF$_2$CF$_3$.
13. A compound of claim 5 wherein X is —CF$_2$CF$_3$.
14. A compound of claim 1 wherein the compound is L-Prolinamide, N-methyl-D-phenylalanyl-N-[3,3,4,4,4-pentafluoro-1-(1H-indol-3-ylmethyl)-2-oxobutyl]-, mono (trifluoroacetate).
15. A composition comprising a compound of claim 1 and a carrier.
16. A pharmaceutical composition comprising a compound of claim 1 and a pharmaceutically acceptable carrier.
17. A method for inhibiting thrombin in a patient in need thereof, said method comprising the administration to said patient of a therapeutically effective amount of a compound of claim 1.
18. A method for treating a patient afflicted with a thrombin condition, said method comprising the administration to said patient of a therapeutically effective amount of a compound of claim 1.
19. A method according to claim 18 wherein said thrombin condition is deep vein thrombosis.
20. A method according to claim 18 wherein said thrombin condition is coronary thrombosis following angioplasty.
21. A method for inhibiting thrombin in blood comprising adding to the blood a composition of claim 15.
22. A method for inhibiting thrombus formation in blood comprising adding to the blood a composition of claim 15.

* * * * *